US012708569B2

(12) United States Patent
Kaiser et al.

(10) Patent No.: US 12,708,569 B2
(45) Date of Patent: Aug. 18, 2026

(54) ABSORBENT ARTICLES WITH UNITARY HOOK FASTENERS, AND METHODS OF MAKING SUCH ARTICLES

(71) Applicant: ATTENDS HEALTHCARE PRODUCTS, INC., Greenville, NC (US)

(72) Inventors: Thomas A. Kaiser, Greenville, NC (US); William S. Sayers, Greenville, NC (US); William W. Gaston, Greenville, NC (US); Trenton T. Ottery, Greenville, NC (US); Alice Tilson Koehler, Greenville, NC (US); Charles F. Schroer, Jr., Greenville, NC (US)

(73) Assignee: Attends Healthcare Products, Inc., Greenville, NC (US)

( * ) Notice: Subject to any disclaimer, the term of this patent is extended or adjusted under 35 U.S.C. 154(b) by 1260 days.

(21) Appl. No.: 16/631,955

(22) PCT Filed: Jul. 20, 2018

(86) PCT No.: PCT/US2018/043011
§ 371 (c)(1),
(2) Date: Jan. 17, 2020

(87) PCT Pub. No.: WO2019/018721
PCT Pub. Date: Jan. 24, 2019

(65) Prior Publication Data

US 2020/0179184 A1 Jun. 11, 2020

Related U.S. Application Data

(60) Provisional application No. 62/535,803, filed on Jul. 21, 2017.

(51) Int. Cl.
*A61F 13/62* (2006.01)
*A61F 13/15* (2006.01)
(Continued)

(52) U.S. Cl.
CPC .. *A61F 13/49015* (2013.01); *A61F 13/15723* (2013.01); *A61F 13/15756* (2013.01);
(Continued)

(58) Field of Classification Search
CPC .......... A61F 13/49015; A61F 13/15723; A61F 13/15756; A61F 13/5616; A61F 13/5633;
(Continued)

(56) References Cited

U.S. PATENT DOCUMENTS

| | | | |
|---|---|---|---|
| 4,548,116 | A | 10/1985 | Yoshida et al. |
| 4,752,351 | A | 6/1988 | Lunt |

(Continued)

FOREIGN PATENT DOCUMENTS

| | | |
|---|---|---|
| EP | 1519828 | 6/2003 |
| EP | 1009249 | 11/2003 |

(Continued)

OTHER PUBLICATIONS

International Search Report and Written Opinion Issued in Corresponding PCT Patent Application No. PCT/US2018/043011, mailed Nov. 9, 2018.

(Continued)

*Primary Examiner* — Catharine L Anderson
*Assistant Examiner* — Lynne Anderson
(74) *Attorney, Agent, or Firm* — Norton Rose Fulbright US LLP

(57) ABSTRACT

This disclosure includes embodiments of disposable absorbent articles and methods of making disposable absorbent articles that include closures with a web of material and hook fasteners that are unitary with the web. For example,
(Continued)

some of the present disposable absorbent articles include diapers or briefs with closure members, such as back ears or front ears, defined at least in part by a nonwoven web with hook fasteners that are unitary with the nonwoven web. Use of such unitary hook fasteners allows simpler construction of such articles and/or softer closure members for improved fit and user comfort, and/or other benefits. Certain embodiments of the present methods can manufacture such absorbent articles with fewer manufacturing steps or processes and/or fewer raw materials, relative to those required to manufacture prior art absorbent articles with hook fastener patches that are added by application of a separate piece of material that includes the hook fasteners.

9 Claims, 18 Drawing Sheets

(51) Int. Cl.
*A61F 13/49* (2006.01)
*A61F 13/56* (2006.01)

(52) U.S. Cl.
CPC ...... *A61F 13/5616* (2013.01); *A61F 13/5633* (2013.01); *A61F 13/625* (2013.01); *A61F 13/5644* (2013.01)

(58) Field of Classification Search
CPC .............. A61F 13/5622; A61F 13/5638; A61F 13/5644; A61F 13/62; A61F 13/622; A61F 13/625; A61F 2013/5683
See application file for complete search history.

(56) References Cited

U.S. PATENT DOCUMENTS 4,794,028 A 12/1988 Fischer
4,857,067 A 8/1989 Wood et al.
4,895,569 A 1/1990 Wilson et al.
4,940,464 A 7/1990 Van Gompel et al.
4,999,067 A 3/1991 Erb et al.
5,624,429 A * 4/1997 Long .................. A61F 13/5622 24/DIG. 11
5,713,111 A 2/1998 Hattori et al.
5,735,984 A 4/1998 Hoff et al.
5,795,640 A 8/1998 Billarant
5,800,672 A 9/1998 Boyce et al.
5,879,494 A 3/1999 Hoff et al.
5,919,493 A 7/1999 Sheppard et al.
5,989,008 A 11/1999 Wytkin
6,054,091 A 4/2000 Miller et al.
6,165,298 A 12/2000 Samida et al.
6,248,276 B1 6/2001 Parellada et al.
6,478,784 B1 11/2002 Johnson et al.
6,481,063 B2 11/2002 Shepard et al.
6,540,497 B1 4/2003 Fuda et al.
6,544,245 B2 4/2003 Neeb et al.
6,645,330 B2 11/2003 Pargass et al.
6,746,434 B2 6/2004 Johnson et al.
6,827,893 B2 12/2004 Clune
6,851,161 B2 2/2005 Kingsford et al.
6,976,978 B2 12/2005 Ruman et al.
6,991,843 B2 1/2006 Armela et al.
7,032,278 B2 4/2006 Kurtz, Jr.
7,048,818 B2 5/2006 Krantz et al.
7,052,636 B2 5/2006 Ausen et al.
7,052,638 B2 5/2006 Clarner et al.
7,056,462 B2 6/2006 Provost et al.
7,172,008 B2 2/2007 Vanbenschoten et al.
7,223,314 B2 * 5/2007 Provost ................. A61F 13/622 156/271
7,275,290 B2 10/2007 Clarner et al.
7,451,532 B2 11/2008 Provost et al.
7,479,195 B2 1/2009 Leidig et al.
7,527,618 B2 5/2009 Benning et al.
7,640,637 B2 1/2010 Efremova et al.
7,727,440 B2 6/2010 Armela et al.
RE42,475 E 6/2011 Armela et al.
7,971,526 B2 7/2011 Blenke et al.
8,236,231 B2 8/2012 Ferguson et al.
8,449,807 B2 5/2013 Ferguson et al.
8,549,714 B1 10/2013 Shepard et al.
8,562,580 B2 10/2013 Van Gompel et al.
8,637,136 B2 1/2014 Ferguson et al.
8,778,243 B2 7/2014 Shepard et al.
8,784,722 B2 * 7/2014 Rocha ................ A44B 18/0049 264/444
9,289,033 B2 3/2016 Cheng
9,398,986 B2 7/2016 Pasqualoni et al.
9,662,248 B2 5/2017 Van Gompel et al.
10,716,718 B2 * 7/2020 O'Connell .......... A61F 13/5622
2002/0016581 A1 * 2/2002 Kline ...................... A61F 13/62 604/389
2003/0041953 A1 3/2003 Farell et al.
2003/0085492 A1 5/2003 Schulte
2004/0020579 A1 * 2/2004 Durrance ............. D04H 13/007 156/290
2004/0261231 A1 12/2004 Jayshree et al.
2006/0247596 A1 * 11/2006 Van Dyke ......... A61F 13/49015 604/385.01
2006/0247597 A1 * 11/2006 Hogan ................ A61F 13/5644 604/391
2006/0265867 A1 11/2006 Schaap et al.
2007/0073260 A1 * 3/2007 Roe ..................... A61F 13/5633 604/389
2009/0299323 A1 * 12/2009 Schlinz ................. A61F 13/565 604/391
2014/0010984 A1 * 1/2014 Bogaerts .................... C09J 7/29 156/228
2014/0358107 A1 * 12/2014 Bader .............. A61F 13/49015 604/385.16
2015/0025492 A1 * 1/2015 Mccabe ............ A61F 13/15747 604/391
2015/0076727 A2 3/2015 Rocha
2015/0173960 A1 * 6/2015 Mansfield ......... A61F 13/51458 604/361
2015/0238369 A1 * 8/2015 Kaiser ..................... A61F 13/53 604/378
2016/0143792 A1 5/2016 Peiffer
2017/0087034 A1 3/2017 Bosser
2017/0181905 A1 * 6/2017 Sakurai ............... A61F 13/5622
2017/0265602 A1 9/2017 Rocha
2018/0050484 A1 * 2/2018 Rocha ................... B29C 59/025
2020/0188188 A1 * 6/2020 Schroer, Jr. ....... A61F 13/15756

FOREIGN PATENT DOCUMENTS

EP 1272398 3/2004
EP 0790884 12/2004
EP 1740142 2/2005
EP 1150585 7/2005
EP 1759606 3/2007
EP 1759607 3/2007
EP 1759608 3/2007
EP 1774866 4/2007
EP 1265507 1/2008
EP 2167301 6/2008
EP 1272139 7/2008
EP 2140775 1/2010
EP 2379308 1/2010
EP 2444225 4/2012
EP 2214525 5/2012
EP 2447048 5/2012
EP 3057752 10/2014

(56) References Cited

FOREIGN PATENT DOCUMENTS

| | | |
|---|---|---|
| WO | WO 2013/147059 | 10/2013 |
| WO | WO 2016/149243 | 9/2016 |

OTHER PUBLICATIONS

Extended European Search Report Issued in Corresponding European Patent Application No. 18836072.1, dated Mar. 19, 2021.

* cited by examiner

ABSORBENT ARTICLES WITH UNITARY HOOK FASTENERS, AND METHODS OF MAKING SUCH ARTICLES

CROSS-REFERENCE WITH RELATED APPLICATIONS

This application is a national phase application under 35 U.S.C. § 371 of International Application No. PCT/US2018/043011, filed Jul. 20, 2018, which claims the benefit of U.S. Provisional Application No. 62/535,803, filed Jul. 21, 2017, the contents of which all of which applications are incorporated herein in their respective entireties.

FIELD OF INVENTION

The present invention relates generally to disposable absorbent articles such as infant diapers, adult incontinence briefs, and sanitary and/or bladder control pads or liners; and more particularly, but not by way of limitation, to such absorbent articles with hook fasteners that are unitary with material that also forms another part of the article, for example a backsheet or closure member, as well as methods of making articles with such unitary hook fasteners.

BACKGROUND

1. Disposable Absorbent Articles and Methods of Manufacture

Examples of disposable absorbent articles that are wearable by a user include baby diapers, training pants, adult incontinence briefs, and sanitary and/or bladder control pads or liners, all of which may be made in disposable forms. "Disposable" refers to articles which are designed to be discarded after a limited use rather than being laundered or otherwise restored for reuse. Disposable absorbent products have met with widespread acceptance in the marketplace for a variety of applications, including infant and adult incontinence care, in view of the manner in which such products can provide effective and convenient liquid absorption and retention while maintaining the comfort of the wearer. Such disposable absorbent articles often include a topsheet that is configured to be closest to the wearer during use, a liquid-impermeable backsheet or outer cover, and an absorbent core between the topsheet and the backsheet. In some instances, such disposable absorbent articles also include an acquisition-distribution layer (ADL) disposed between the topsheet and the absorbent core.

One example of such a disposable absorbent article is shown in FIGS. 1 and 2, which depicts a lower plan view of a prior art diaper 10. Diaper 10 includes a chassis 14 having a front waist portion 18, an opposing rear waist portion 22, and a crotch portion 26 extending longitudinally between front and rear waist portions 18, 22. Chassis 14 further includes an outer surface 30 configured to face away from a wearer during use of the diaper, and an opposing body facing surface 34 configured to face a wearer during use of the diaper. In the view of FIG. 1, a dashed leader extends from the outer surface to reference numeral 30 because outer surface 30 is opposite body facing surface 34 and therefore not visible in FIG. 1.

As shown in FIG. 1, diaper 10 further includes a pair of closure members 38 configured to couple rear waist portion 22 to front waist portion 18 in a well-known configuration in which a left side 42 of the chassis defines a first leg opening for a wearer's left leg, and in which a right side 46 of the chassis defines a second leg opening for the wearer's right leg. As will be appreciated by those of ordinary skill in the art, in the depicted configuration in which the closure members are coupled to the rear waist portion of the chassis, closure members 38 may be referred to as "back ears" or "back ear closure members." In the depicted configuration, the closure members include a pair of elasticized panels 50 each having a first end 54 bonded to rear waist portion 22 of chassis 14, and a second end 58 shown extending away from rear waist portion 22. "Bonded" refers to the joining, adhering, connecting, attaching, or the like, of two elements. Two elements will be considered to be bonded together when they are bonded directly to one another or indirectly to one another, such as when each is directly bonded to intermediate elements.

Each closure member 38 further includes a tape tab 62 with a first end 66 bonded to back ear 50, a second end 70 shown extending laterally outward from back ear 50, and a fastener patch 74 coupled to the tape tab. Back ears 50 are each formed of a stretchable elastic material, such as a nonwoven laminate, that permits adjustments in the length and tension of back ears 50 to vary the form and fit of diaper 10 when worn by a user. Tape tabs 62 are typically formed of an inelastic nonwoven material and carry fastener patches 74. Fastener patches 74 include patches of hook material configured to interact with a corresponding loop material in the well-known hook-and-loop fastener arrangement. Hook and loop fasteners are mechanical fasteners that include hooks, such as in a hook fastener portion, that are configured to engage loops in a loop fastener portion or in fibers of a sheet of fabric; for example, a nonwoven or woven fabric with fibers that define open or loop-like regions into which the hooks can extend and engage. Examples of such hook and loop fasteners may be referred to as VELCRO. Connection of closure members 38 to front waist portion 18 is facilitated by a landing zone 78 configured to be engaged by fastener patches 74. In this embodiment, landing zone 78 is defined by an anchoring member that includes a patch of loop material bonded to front waist portion 18 of chassis 14, for example, to the backsheet, and configured to be engaged by the hook material of fastener patches 74.

As shown in FIG. 1, diaper 10 also includes a pair of front ears 82 extending from opposite sides 42, 46 of chassis 14 with each of front ears 82 each having a first end 86 bonded to front waist portion 18 of chassis 14, and a second end 90 shown extending away from a respective side of front waist portion 18. Front ears 82 are each formed of a relatively soft nonwoven material and is configured to be overlapped by the corresponding tape tab 62 and/or back ear 50 to prevent the edges of tape tab 62 from pinching, rubbing, or otherwise irritating a user's skin in use when fastener patches 74 are engaged with landing zone 78 to couple rear waist portion 22 to front waist portion 18.

The material used for tape tabs 62 and/or the hook material typically used for fastener patches 74 may be relatively rigid and their edges, ends, and/or rough surfaces may scratch or otherwise irritate a user's skin when the diaper is being put onto a user or, if the back ear 50 and tape 62 are not positioned correctly, while the diaper is worn by a user. This risk of irritation is further increased with adult incontinence absorbent articles, such as briefs, because adults are more likely to wear additional cloth undergarments over the incontinence brief, which can impart further pressure urging the tapes 62 and fastener patches 74 toward a wearer's skin. Users of adult incontinence garments may also be more sensitive to such irritation, because such users may have softer skin be sometimes associated with aging.

In a disposable article of the type shown in FIGS. 1 and 2, and shown particularly in FIG. 2, outer surface 30 is typically defined by a water-impermeable backsheet 94, and body facing surface 34 is typically defined by a water-permeable topsheet 98. As also shown, diaper 10 also includes an absorbent core 102 and, in the depicted embodiment, an acquisition-distribution layer or "ADL" 106 disposed between absorbent core 102 and topsheet 98. "Layer" when used in the singular can be a single element or a plurality of elements. For example, a plurality of sheets may together define a single layer, such as, for example, a layer with a particular function to which the sheets of the layer contribute. "Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. "Lamination" is the technique of manufacturing a material in multiple layers, so that the composite material has benefits of all the combined layers, such as, for example, improved mechanical strength or durability, improved stability, lower permeability to water, and/or other properties. A laminate is a permanently assembled object by heat, pressure, welding, or adhesives.

Liquid-impermeable backsheet 94 can include, for example, an inner liquid-impermeable film and an outer nonwoven backsheet that can be a nonwoven fabric. A "film" is a membrane-like layer of material formed of one or more polymers, which does not have a form consisting predominately of a web-like structure of fibers and/or other fibers. In some embodiments of the present articles, backsheet or outer cover 104 can be breathable, for example, an inner liquid-impermeable film of backsheet 104 can comprise a breathable film. The terms "breathable," "breathable film," "breathable laminate" or "breathable outer cover material" or "breathable backsheet" refers to a film, laminate, or outer cover material having a water vapor transmission rate ("WVTR") of at least about 300 grams/$m^2$/24 hours. Breathable materials typically rely on molecular diffusion of vapor, and are substantially liquid impermeable. "Nonwoven" fabrics, according to an INDA definition, are broadly defined as sheet or web structures bonded together by entangling fiber or filaments (and by perforating films) mechanically, thermally, or chemically. They are flat, porous sheets that are made directly from separate fibers or from molten plastic or plastic film. They are not made by weaving or knitting and do not require converting the fibers to yarn. The basis weight of nonwoven fabrics is usually expressed as gsm or grams per square meter. "Nonwoven backsheet" is a backing substrate layer in the outer cover; a nonwoven backsheet is most often a nonwoven layer facing away from the wearer.

An "absorbent core" is a structure typically disposed between a topsheet and backsheet of an absorbent article and containing materials like SAP and/or cellulosic fibers that are configured to absorb liquid in the absorbent article. The absorbent core may also include a cover layer or envelope material. The cover layer or envelope may comprise; nonwovens, SAP, cellulosic or non-cellulosic materials, films, fibers or substrate made of any one two or all of these combination materials. "Superabsorbent" or "superabsorbent material" or "SAP" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The SAP materials can be natural, synthetic and modified natural polymers and materials. In addition, the SAP materials can be inorganic materials, such as silica gels, or organic compounds such as cross linked polymers.

The prior art diaper configuration of FIGS. 1 and 2 is relatively complex in that each closure member 38 includes a number of components—including back ear 50, tape tab 62, and fastener patch 74—that must be assembled during manufacture. As described in more detail below, this combination of components requires a number of steps in the process of manufacturing diaper 10, which complexity increases the cost and complexity of manufacturing, which complexity also increases the risk of errors and malfunctions. As shown in FIGS. 3 and 4, strips of hook fastener material 110 are typically bonded to a nonwoven web 114, and the joined web and hook fastener material cut along lines 118 to define tape tabs 62. Each such tape tab 62 is typically then bonded to a portion of an elasticized web 122 as shown in FIG. 3, from which individual elastic panels 50 are cut along lines 126 to define closure members 38 such as those described above and shown in FIG. 1. All or a portion of web 122, for example between but not extending to ends 54 and 58, can be elasticized with a plurality of elastic strands 130 as shown, or in other embodiments, additionally or alternatively with an elastic film. As will be appreciated by those of ordinary skill in the art, the processes of bonding hook fastener material 110 to web 114, cutting web 114, bonding tape tab 62 to elasticized web 122, and cutting web 122 may all be performed on the same manufacturing floor and, in some instances, on the same manufacturing line. In addition to the relatively complex manufacturing process required to assemble closure members 38 and bond them to chassis 14, the bonds between fastener patch 74 may sometimes degrade, resulting in fastener patch 74 partially or entirely detaching from tape tab 62, which can result in protruding edges that can irritate a user's skin and/or complete failure of diaper 10.

FIGS. 5A-5C depict plan views of a back ear closure member 38 manufactured by the processes described above with reference to FIGS. 3 and 4. As annotated in FIG. 5A, closure member 38 has an overall width 134. As indicated by arrows 138 in FIG. 5B, the primary force to which closure member 38 is subjected during use is tension between first end 54 of elastic panel 50, at which the closure member is bonded to the rear waist portion, and second end 70 of tape tab 62, at which the closure member is coupled to the front waist portion. However, as indicated by arrow 142 in FIG. 5C, closure member 38 and particularly tape tab 62 may also be subject to torque around fastener patch 74. This torque may result in uneven loading along the height of first end 54 of elastic panel 50 and, as a result, may require a greater number of elastic strands 130, or elastic strands of larger size or decitex, that might be required if the torque were not fully transmitted to first end 54 of the elastic panel.

2. Ultrasonic Formation of Hook Fasteners

FIG. 6 depicts a conceptual side view of a prior art system 150 for forming hook fasteners that are unitary with a web 154 of material, such as a polymer nonwoven. As shown, web 154 is disposed between a sonotrode 158 and a proximal surface 162 of a tool 166 such that a first side 170 of the web contacts the proximal surface of the tool. Tool 166 defines a plurality of cavities 174, each of which cavities 174 extending from a base 178 at the proximal surface to a distal end 182 within the tool to define a negative mold of a hook fastener. By way of example, FIG. 6 depicts tool as a rotating anvil, whereas other embodiments can include a tool with any of various shapes or configurations. Sonotrode 158 is configured to vibrate, for example at one or more ultrasonic frequencies, to locally heat web 154 to cause the polymer of the web to flow into the cavities. Thus, once the web is disposed between the sonotrode and the tool, ultrasonic energy is delivered from the sonotrode to the web such that a temperature of the first side of the web increases above the polymer's glass transition temperature. Thereafter or simultaneously, the web can be compressed between the sonotrode and the tool such that polymer of the web flows into the cavities until the polymer substantially fills the cavities to form a plurality of hook fasteners 186 on first side 170 of the web that are unitary with the web.

Additional details of hook fastener shapes, and tools and methods for forming such hooks, are disclosed in U.S. Pat. No. 8,784,722, which is incorporated by reference. For example, FIGS. 2-2N of U.S. Pat. No. 8,784,722 depicts a plurality hook fastener shapes.

SUMMARY

This disclosure includes embodiments of disposable absorbent articles and methods of making disposable absorbent articles that include closures with a web of material and hook fasteners that are unitary with the web. For example, some of the present disposable absorbent articles include diapers or briefs with closure members, such as back ears or front ears, defined at least in part by a nonwoven web with hook fasteners that are unitary with the nonwoven web. The use of such unitary hook fasteners allows simpler construction of such articles and/or softer closure members for improved fit and user comfort, and/or other benefits. Certain embodiments of the present methods can manufacture such absorbent articles with fewer manufacturing steps or processes and/or fewer raw materials, relative to those required to manufacture prior art absorbent articles with hook fastener patches that are added by application of a separate piece of material that includes the hook fasteners. Such simplified methods not only can reduce cost and time required for manufacturing, but can also reduce the number of steps or processes at which errors can occur, thereby increasing efficiency of uptime of manufacturing lines. Additionally, the forming of unitary hook fasteners in-line during the process of manufacturing an absorbent article can provide improved opportunities to configure the hook fasteners for a particular application; for example, relatively taller hooks with relatively larger spacing may perform better for engaging a loop fastener material, whereas relatively shorter hooks at relatively smaller spacing may perform better if the hook fasteners engage a nonwoven (spunbond) backsheet.

Additional embodiments of the present disposable absorbent articles include sanitary and/or bladder control pads or liners with hook fasteners that are unitary with a backsheet of the pad or liner to retain the pad or liner in a desired position relative to a user's garment. Certain embodiments of the present methods can manufacture such pads or liners with fewer manufacturing steps or processes and/or fewer raw materials, relative to those required to manufacture prior art absorbent articles with adhesives or hook fastener patches that are added by application of a separate piece of material that includes the hook fasteners.

Some embodiments of the present disposable absorbent articles comprise: a chassis having opposing front and rear waist portions, a crotch portion extending longitudinally between the front and rear waist portions, a body facing surface configured to face a wearer during use of the article, and an outer surface configured to face away from a wearer during use of the article; two closure members each having a first end, a second end, and a width extending between the first and second ends, each of the closure members having an elasticized portion and a nonwoven panel with at least one fastener region on a body facing side of the nonwoven panel, each fastener region comprising a plurality of hook fasteners that are unitary with the nonwoven panel; where the first end of each closure member is bonded to the rear waist portion of the chassis, and the second end of each closure member is configured to overlap and be releasably coupled to the front waist portion to define a closed configuration in which: the front and rear waist portions cooperate with the closure members to encircle and define a waist opening, a left side of the chassis defines a first leg opening, and a right side of the chassis defines a second leg opening.

In some embodiments of the present disposable absorbent articles, each fastener region comprises a plurality of distinct sub-regions of the hook fasteners. In some embodiments, the elasticized portion of each of the closure members is defined by an elastic panel having a first end defining the first end of the closure member, a second end, and a width extending between the first and second ends, and the nonwoven panel of each of the closure members defines a fastener tab having a first end bonded to the elastic panel, and a second end defining a second end of the closure member such that the width of the closure member extends from the first end of the elastic panel to the second end of the fastener tab. In some embodiments, the nonwoven panel of each of the closure members includes the respective elasticized portion. In some embodiments, the nonwoven panel of each of the closure members includes a plurality of the fastener regions spaced along a portion of the width of the closure member. In some embodiments, the fastener regions of each of the closure members comprise a first fastener region having a first height, and a second fastener region having a second height and disposed between the elasticized portion and the first fastener region, and the second height is greater than the first height. In some embodiments, the fastener regions of each of the closure members are closer to the second end of the closure member than to the first end of the closure member.

Some embodiments of the present disposable absorbent articles further comprise: two nonwoven front-ear members each having a first end, a second end, and a width extending between the first and second ends, each of the front-ear members having at least one fastener region on an outward-facing side of the front-ear member, each fastener region comprising a plurality of hook fasteners that are unitary with the nonwoven front-ear panel; where the first end of each front-ear member is bonded to the front waist portion of the chassis, and the second end of each closure member is configured to be overlapped by and be releasably coupled to a body-facing side of a corresponding one of the closure members when the closure members are coupled to the front waist portion. In some embodiments, the at least one fastener region of each of the front-ear members includes a plurality of the fastener regions spaced along a portion of the width of the front-ear member. In some embodiments, the fastener regions of each of the front-ear members are closer to the second end of the front-ear member than to the first end of the front-ear member. In some embodiments, at least a portion of the fastener regions of the front-ear members are spaced inward from a peripheral edge of the respective front-ear member.

Additional embodiments of the present disposable absorbent articles comprise: a chassis having opposing front and rear waist portions, a crotch portion extending longitudinally between the front and rear waist portions, a body facing surface configured to face a wearer during use of the article, and an outer surface configured to face away from a wearer during use of the article; two nonwoven front-ear members each having a first end, a second end, and a width extending between the first and second ends, each of the front-ear members having at least one fastener region on an outward-facing side of the front-ear member, each fastener region comprising a plurality of hook fasteners that are unitary with the nonwoven front-ear panel; and two closure members each having a first end, a second end, and a width extending between the first and second ends, each of the closure members having an elasticized portion and a nonwoven panel with at least one fastener region on a body facing side of the nonwoven panel, each fastener region comprising a plurality of hook fasteners; where the first end of each closure member is bonded to the rear waist portion of the chassis, and the second end of each closure member is configured to overlap and be releasably coupled to the front waist portion to define a closed configuration in which: the front and rear waist portions cooperate with the closure members to encircle and define a waist opening, a left side of the chassis defines a first leg opening, and a right side of the chassis defines a second leg opening; and where the first end of each front-ear member is bonded to the front waist portion of the chassis, and the second end of each closure member is configured to be overlapped by and be releasably coupled to a body-facing side of a corresponding one of the closure members when the closure members are coupled to the front waist portion.

In some embodiments of these additional disposable absorbent articles, each fastener region comprises a plurality of distinct sub-regions of the hook fasteners. In some embodiments, the elasticized portion of each of the closure members is defined by an elastic panel having a first end defining the first end of the closure member, a second end, and a width extending between the first and second ends, and the nonwoven panel of each of the closure members defines a fastener tab having a first end bonded to the elastic panel, and a second end defining a second end of the closure member such that the width of the closure member extends from the first end of the elastic panel to the second end of the fastener tab. In some embodiments, the nonwoven panel of each of the closure members includes the respective elasticized portion. In some embodiments, the nonwoven panel of each of the closure members includes a plurality of the fastener regions spaced along a portion of the width of the closure member. In some embodiments, the fastener regions of each of the closure members are closer to the second end of the closure member than to the first end of the closure member. In some embodiments, at least a portion of the fastener regions are spaced inward from a peripheral edge of the respective closure member. In some embodiments, the hook fasteners of each of the nonwoven front-ear members are unitary with the nonwoven front-ear member.

In some embodiments of the present disposable absorbent articles, a landing portion of the outer surface on the front waist portion of the chassis is configured to be releasable engaged by the fastener portions of the closure members. In some embodiments, the portion of the outer surface is defined by an anchoring member bonded to a backsheet of the chassis. In some embodiments, the anchoring member comprises a loop fastener material. In some embodiments, at least a portion of the fastener regions are spaced inward from a peripheral edge of the respective closure member.

In some embodiments of the present disposable absorbent articles, the front waist portion, rear waist portion, and crotch portion are defined by corresponding regions of a common chassis member. In some embodiments, the chassis comprises a topsheet, a backsheet bonded to the topsheet, and an absorbent core disposed between the topsheet and the backsheet.

In some embodiments of the present methods of making a disposable absorbent article, the method comprises: disposing a nonwoven polymer web between a sonotrode and a proximal surface of a tool such that a first side of the web contacts the proximal surface of the tool, the tool defining a plurality of cavities, each of the cavities extending from a base at the proximal surface to a distal end within the tool to define a negative mold of a hook fastener; delivering ultrasonic energy from the sonotrode to the web such that a temperature of the first side of the web increases above the polymer's glass transition temperature; compressing the web between the sonotrode and the tool such that polymer of the web flows into the cavities until the polymer substantially fills the cavities to form a plurality of hook fasteners on the first side of the web that are unitary with the web, the plurality of hook fasteners disposed in at least one fastener region; and cutting the web in at least one direction laterally across the or between the fastener region(s) to define a fastener member having a first end, a second end, and a fastener region between the first and second ends; and coupling the first end of the fastener member to a front or rear waist portion of a chassis of a disposable absorbent article; where the disposing, delivering, compressing, cutting, and coupling are performed on the same manufacturing floor.

In some embodiments of the present methods, each fastener region comprises a plurality of distinct sub-regions of the hook fasteners. In some embodiments, the disposing, delivering, compressing, cutting, and coupling are performed on the same manufacturing line. In some embodiments, the fastener region of the fastener member is closer to the second end of the fastener member than to the first end of the fastener member. In some embodiments, the web is not elasticized. In some embodiments, coupling comprises bonding the first end of the fastener member to a second end of an elastic panel, and bonding a second end of the elastic panel to the front waist portion. In some embodiments, the web has a width and a length that is at least five times longer than the width, the longitudinal axis of each of the fastener region(s) is parallel to the length.

In some embodiments of the present methods, the fastener region(s) extends along a majority of the length of the web. In some embodiments, first and second portions of the web are elasticized, the first elasticized portion is on a first lateral side of the fastener region(s), the second elasticized portion is on a second lateral side of the fastener region(s), and the cutting is performed such that a portion of the first elasticized portion is disposed between the first end of the fastener member and the fastener region. In some embodiments, coupling comprises bonding a first end of the fastener portion to a rear waist portion of a chassis of a disposable absorbent article. In some embodiments, the fastener region(s) comprise: at least one medial fastener region; at least one first lateral fastener region on a first lateral side of the medial fastener region(s); and at least one second lateral fastener region on a second lateral side of the medial fastener region(s). In some embodiments, the at least one medial fastener region comprises a plurality of medial fastener regions; the at least one first lateral fastener region comprises a plurality of first lateral fastener regions; and the at least one second lateral fastener region comprises a plurality of second lateral fastener regions. In some embodiments, each of the first lateral fastener regions is elongated, each of the second lateral fastener regions is elongated, and cutting the web comprises cutting sequentially: laterally inward from a first lateral edge of the web; laterally inward between a first one and second one of the first lateral fastener regions; around a first one of the medial fastener regions; and laterally outward between the second one and a third one of the first lateral fastener regions; and laterally outward to the first lateral edge of the web to separate the fastener member from the web. In some embodiments, the fastener member is a first fastener member, and cutting the web comprises cutting sequentially: laterally inward from a second lateral edge of the web; laterally inward between a first one and second one of the second lateral fastener regions; around a second one of the medial fastener regions; and laterally outward between the second one and a third one of the second lateral fastener regions; and laterally outward to the second lateral edge of the web to separate a second fastener member from the web. In some embodiments, the cutting is performed such that there is no wasted web between the first and second fastener members. In some embodiments, coupling comprises bonding a first end of the fastener portion to a rear waist portion of a chassis of a disposable absorbent article.

In some embodiments of the present disposable absorbent pad or liner for a garment, the pad or liner comprising: a chassis having a front portion, a rear portion, and a crotch portion between the front and rear portions, the chassis including a liquid-permeable topsheet having a body-facing side configured to face a wearer when the article is in use, a liquid-impermeable backsheet having an outer side configured to face away from the wearer when the article is in use, and an absorbent core disposed between the topsheet and the backsheet; where the backsheet comprises an outermost layer with at least one fastener region on the outer side of the chassis, each fastener region comprising a plurality of hook fasteners that are unitary with the outermost layer. In some embodiments, each fastener region comprises a plurality of distinct sub-regions of the hook fasteners. In some embodiments, the fastener region(s) span a majority of a surface area of the outer side of the chassis. In some embodiments, the fastener region(s) comprise a plurality of fastener regions. In some embodiments, the chassis includes at least one pair of lateral wing panels each including an additional fastener region. In some embodiments, the at least one pair of lateral wing panels includes a pair of lateral wing panels extending outward from opposing lateral sides of the crotch portion of the chassis. In some embodiments, the fastener regions of each lateral wing panel is spaced inward from a peripheral edge of the respective lateral wing panel. In some embodiments, the outermost layer of the backsheet comprises a nonwoven.

In some embodiments of the present methods of making a disposable absorbent pad or liner for a garment, the method comprises: disposing a nonwoven polymer web between a sonotrode and a proximal surface of a tool such that a first side of the web contacts the proximal surface of the tool, the tool defining a plurality of cavities, each of the cavities extending from a base at the proximal surface to a distal end within the tool to define a negative mold of a hook fastener; delivering ultrasonic energy from the sonotrode to the web such that a temperature of the first side of the web increases above the polymer's glass transition temperature; compressing the web between the sonotrode and the tool such that polymer of the web flows into the cavities until the polymer substantially fills the cavities to form a plurality of hook fasteners on the first side of the web that are unitary with the web, the plurality of hook fasteners disposed in at least one fastener region; cutting the web across the or between the fastener region(s) to separate a portion of the web that includes at least a portion of at least one of the fastener region(s); and bonding the web portion to a liquid-permeable topsheet, with an absorbent core disposed between the web portion and the liquid-permeable topsheet, to define the article such that the web portion forms a backsheet of the article. In some embodiments, each fastener region comprises a plurality of distinct sub-regions of the hook fasteners.

In some embodiments of the present methods, the disposing, delivering, compressing, cutting, and bonding are performed on the same manufacturing floor. In some embodiments, the disposing, delivering, compressing, cutting, and bonding are performed on the same manufacturing line. In some embodiments, the web portion includes a front portion, a rear portion, and a crotch portion between the front and rear portions. In some embodiments, the fastener region(s) span a majority of a surface area of the outer side of the web portion. In some embodiments, the fastener region(s) comprise a plurality of fastener regions. In some embodiments, the article includes at least one pair of lateral wing panels each including an additional fastener region. In some embodiments, the at least one pair of lateral wing panels includes a pair of lateral wing panels extending outward from opposing lateral sides of the crotch portion of the article. In some embodiments, the fastener regions of each lateral wing panel is spaced inward from a peripheral edge of the respective lateral wing panel.

Some embodiments of the present disposable absorbent articles comprise: a chassis having opposing front and rear waist portions, a crotch portion extending longitudinally between the front and rear waist portions, a body facing surface configured to face a wearer during use of the article, and an outer surface configured to face away from a wearer during use of the article; two rear closure members each having a first end, a second end, and a width extending between the first and second ends, and a height extending perpendicular to the width, each of the rear closure members comprising an elasticized portion and a nonwoven panel; two front closure members each having a first end, a second end, and a width extending between the first and second ends, and a height extending perpendicular to the width, each of the front closure members comprising an elasticized portion and a nonwoven panel; where the first end of each rear closure member is bonded to the rear waist portion of the chassis, the first end of each front closure member is bonded to the front waist portion of the chassis, and the second end of each rear closure member is configured to overlap and be releasably coupled to the second end of a corresponding one of the front closure members to define a closed configuration in which: the front and rear waist portions cooperate with front and rear the closure members to encircle and define a waist opening, a left side of the chassis defines a first leg opening, and a right side of the chassis defines a second leg opening; and where each of the front closure members and/or the rear closure members includes at least one fastener region on the respective nonwoven panel, each fastener region comprising a plurality of hook fasteners that are unitary with the nonwoven panel and configured to releasably couple the second end of each front closure member to the second end of the corresponding one of the front closure members.

In some embodiments of the present disposable absorbent articles, each of the fastener regions comprises a plurality of distinct sub-regions of the hook fasteners. In some embodiments, the elasticized portion of each of the closure members is defined by an elastic panel having a first end defining the first end of the closure member, a second end, and a width extending between the first and second ends, and the nonwoven panel of each of the closure members has a first end bonded to the elastic panel, and a second end defining a second end of the closure member such that the width of the closure member extends from the first end of the elastic panel to the second end of the fastener tab. In some embodiments, the nonwoven panel of each of the closure members includes the respective elasticized portion. In some embodiments, the nonwoven panel of each of the closure members includes a plurality of the fastener regions spaced along a portion of the height of the closure member. In some embodiments, the fastener regions of each of the respective closure members are closer to the second end of the closure member than to the first end of the closure member. In some embodiments, at least a portion of the fastener regions are spaced inward from a peripheral edge of the respective closure member. In some embodiments, the front waist portion, rear waist portion, and crotch portion are defined by corresponding regions of a common chassis member. In some embodiments, the chassis comprises a topsheet, a backsheet bonded to the topsheet, and an absorbent core disposed between the topsheet and the backsheet.

The term “coupled” is defined as connected, although not necessarily directly, and not necessarily mechanically; two items that are “coupled” may be unitary with each other. The terms “a” and “an” are defined as one or more unless this disclosure explicitly requires otherwise. The term “substantially” is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term “substantially” may be substituted with “within [a percentage] of” what is specified, where the percentage includes 0.1, 1, 5, and 10 percent.

The terms “comprise” and any form thereof such as “comprises” and “comprising,” “have” and any form thereof such as “has” and “having,” and “include” and any form thereof such as “includes” and “including” are open-ended linking verbs. As a result, an apparatus that “comprises,” “has,” or “includes” one or more elements possesses those one or more elements, but is not limited to possessing only those elements Likewise, a method that “comprises,” “has,” or “includes” one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term “consisting of” or “consisting essentially of” can be substituted for any of the open-ended linking verbs recited above, in order to change the scope of a given claim from what it would otherwise be using the open-ended linking verb.

Further, a device or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. Views in the figures are drawn to scale, unless otherwise noted, meaning the sizes of the depicted elements are accurate relative to each other for at least the embodiment in the view. Views described as conceptual are not necessarily drawn to scale.

DETAILED DESCRIPTION OF ILLUSTRATIVE EMBODIMENTS

In some embodiments of the present methods of making disposable absorbent articles, the method comprises: disposing a nonwoven polymer web between a sonotrode, for example sonotrode 158, and a proximal surface of a tool defining a plurality of negative molds of hook fasteners, for example proximal surface 162 of tool 166, such that a first side, for example 170, of the web contacts the proximal surface of the tool. Such methods further comprise delivering ultrasonic energy from the sonotrode to the web such that a temperature of the first side of the web increases above the polymer's glass transition temperature; and compressing the web between the sonotrode and the tool such that polymer of the web flows into the cavities until the polymer substantially fills the cavities to form a plurality of hook fasteners on the first side of the web that are unitary with the web.

Figure 7:
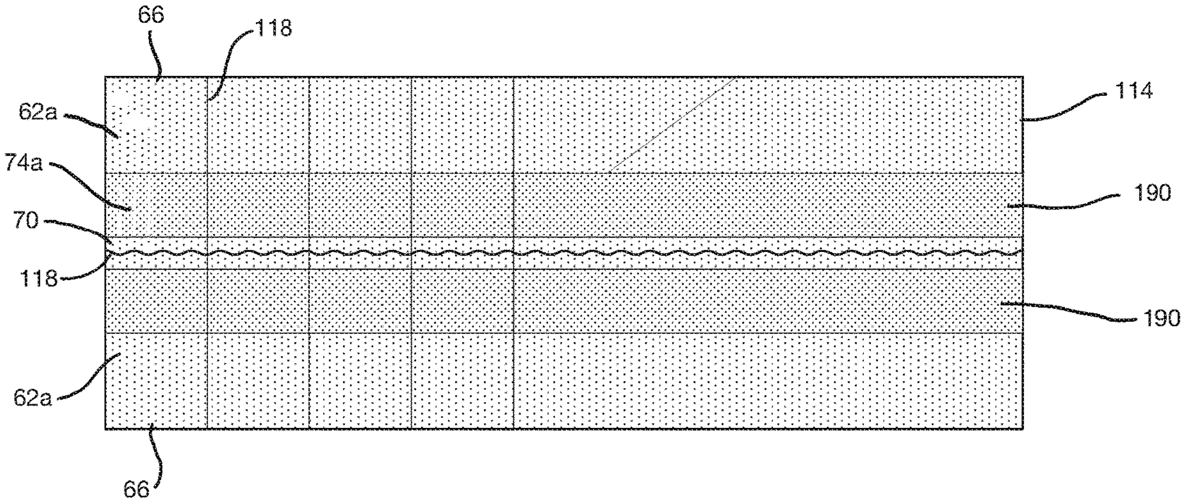
FIG. 7 depicts a plan view of a web of material illustrating a first embodiment of a method of manufacturing fastener members that may be used in absorbent articles.

By way of example, FIG. 7 depicts a plan view of a web of material illustrating one embodiment of a method of manufacturing fastener members, specifically tape tabs 62*a*, that may be used in absorbent articles. In this embodiment, rather than bonding a separate hook fastener material 110 to non-elasticized web 114, web 114 is disposed between a sonotrode and an appropriate tool, for example tool 166, and energy delivered and the web compressed as described above, to define a plurality of hook fasteners in two fastener regions 190 that extend the length of web 114 as shown. Tool 166, and specifically recesses 174 can be provided in a pattern corresponding to the desired pattern of fastener regions 190. For example, to form the embodiment shown in FIG. 7, tool 166 would include two substantially continuous rows of recesses 174 around the perimeter of tool 166.

Some embodiments of the present methods further comprise cutting the web in at least one direction laterally across the or between the fastener region(s) 110 to define one or more fastener members each having a first end 66, a second end 70, and a fastener region 74*a* that is closer to the second end than to the first end. For example, as shown in FIG. 7, once the hook fasteners are formed in fastener regions 110, web 114 can be cut in similar fashion to the prior art method described above; specifically, along lines 118—laterally across fastener regions 110 and longitudinally between fastener regions 110—to define a plurality of tape tabs 62*a* that can be used in place of tape tabs 62 described above. While fastener regions 190 are shown spanning the entire length of web 114, which length is typically much greater than the width of the web, other embodiments may include fastener regions 190 that span less than all but still a majority of the length of the web. For example, in some embodiments, distinct fastener regions 190 are applied to each longitudinal segment of web 114 that will form a separate tape tab 62*a* such that, after the web is cut, fastener region 74*a* of each tape tab 62*a* will be spaced apart from the respective edges of the tape tab.

Some embodiments of the present methods further comprise coupling the first end of the fastener member to a front or rear waist portion of a chassis of a disposable absorbent article. For example, in the embodiment shown in FIG. 7, once tape tabs 62*a* are separated from web 114, first end 66 of each tape tab 62*a* can be bonded to second end 58 of a corresponding elastic panel 50, the first end (54) of which elastic panel 50 can then be bonded to rear waist portion 18 of a chassis 14.

In some embodiments of the present methods, the foregoing disposing, delivering, compressing, cutting, and coupling steps are performed on the same manufacturing floor and/or on the same manufacturing line. In particular, the formation of hook fasteners by the present methods permit the formation of the hook fasteners on the same manufacturing floor or even in the same manufacturing line on which the rest of the absorbent article is assembled. In contrast to prior art methods in which hook fastener materials are obtained from a supplier, or at least from a separate manufacturing facility or line, and bonded to tape tabs, the present methods permit the more-efficient option of on-site formation of hooks that are unitary with a web of material that would be included in the absorbent article anyway, thereby eliminating the need for the additional hook fastener material.

Figure 8:
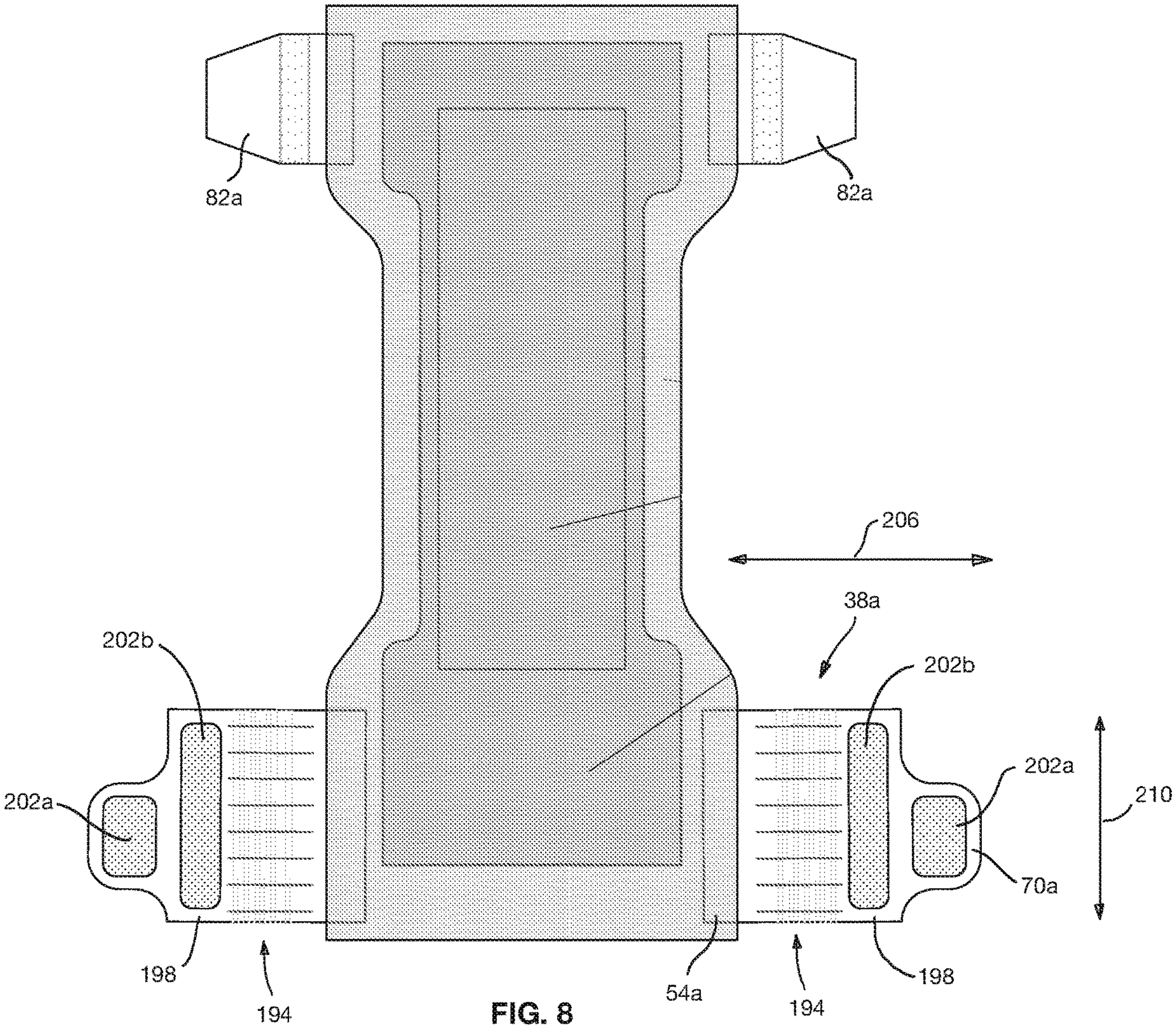
FIG. 8 depicts a top plan view of a first embodiment of the present disposable absorbent articles, specifically a diaper, in an open configuration.
Figure 9:
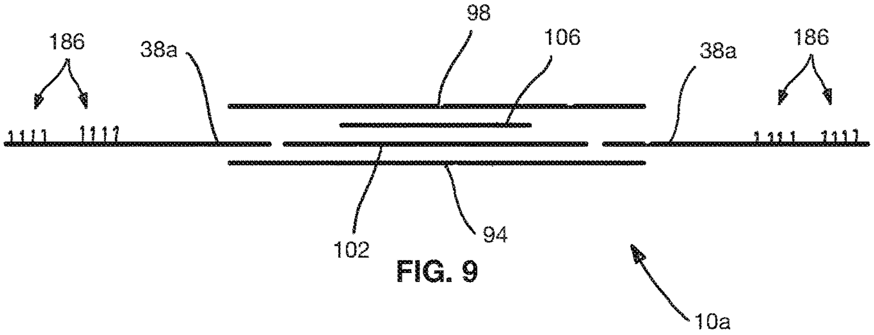
FIG. 9 depicts an exploded end view of the diaper of FIG. 8.

Referring now to FIGS. 8 and 9; FIG. FIG. 8 depicts a top plan view of a first embodiment 10*a* of the present disposable absorbent articles, specifically a diaper, in an open configuration; and FIG. 9 depicts an exploded end view of rear waist portion 18 of diaper 10*a*. Diaper 10*a* is substantially similar in many respects to diaper 10, and the differences in diaper 10*a* relative to diaper 10 will therefore be described here. Specifically, diaper 10*a* includes back ear closure members 38*a* that differ relative to back ear closure members 38 of diaper 10, and includes front ears 82*a* that differ relative to front ears 82 of diaper 10. In other embodiments, however, diaper 10 may include only the modified closure members 38*a* or only the modified front ears 82*a*.

As shown in FIG. 8, each closure members 38*a* has an elasticized portion 194 and a nonwoven panel 198 with at least one fastener region 202 on a body facing side 34 of the nonwoven panel. As used in this disclosure, the terms "elasticized," "stretch," and "stretchable" are used interchangeably to define a material or composite that can be elongated by at least 25% of its relaxed length, i.e., elongated to at least 1¼ times its relaxed length (an elongation of 25%), and that will recover upon release of the applied force at least 10% of its elongation. According to this definition, upon release of the applied force at 25% elongation, the material or composite must recover to at least about a 15% or less elongation. For example, a material or composite is deemed to be "stretchable" if a sample length of 100 centimeters can be elongated to a length of at least 125 centimeters, and upon release of the applied force recovers to a length of not more than about 115 centimeters. Many elastic or stretchable materials or composites can be elongated by more than 25% of their relaxed length, and many of these will recover to, or close to, their original relaxed length upon release of the applied force. These materials can include not only webs of elastic or stretchable films, such as cast or blown films, but also nonwoven fibrous elastic webs such as meltblown elastomeric fibrous nonwoven webs. "Elastic," "elasticized" and "elasticity" mean that property of a material by virtue of which it tends to recover its original size and shape after removal of a force causing a deformation.

In some embodiments, such as the one shown, the nonwoven panel of each closure member 38*a* includes a plurality of the fastener regions spaced along a portion of the width, measured in direction 206, of the closure member. For example, in the depicted embodiment, each closure member 38*a* includes a first fastener region 202*a* and a second fastener region 202*b* disposed between first fastener region 202*b* and elasticized portion 194. In some configurations, such as the one shown, second fastener region 202*b* can have a greater height, measured in direction 210, than that of first fastener region 202*a*. Each fastener region 202 comprises a plurality of hook fasteners 186 that are unitary with nonwoven panel 198. As with closure members 38, fastener regions 202*a* and 202*b* of each closure member 38*a* are closer to a second end 70*a* of the closure member than they are to a first end 54*a* of the closure member. In the depicted embodiment, nonwoven panel 198 includes elasticized portion 194; for example, nonwoven panel 198 spans and defines the entirety of closure member 38*a*; specifically, a portion of nonwoven panel 198 is elasticized, for example with elastic strands and/or elastic film, to define elasticized portion 194. In some such embodiments, at least a portion of the fastener regions 202 are spaced inward from a peripheral edge of the respective closure member. For example, in the embodiment shown in FIG. 8, the entire perimeters of fastener regions 202*a* and 202*b* are spaced inward from a peripheral edge of the corresponding closure member. This spacing can, for example, result in closure members that are perceived by users as softer and more compliant because, for example, the edges of the closure member do not include and/or are not directly bordered by relatively rigid hook fasteners that may tickle, scratch, or otherwise irritate a user's skin.

As shown in FIG. 9, the inclusion of elasticized portion 194 and unitary hook fasteners 186 on nonwoven panel 198 of closure member 38 simplifies the construction of diaper 10*a* relative to that of diaper 10. Specifically, rather than three separate pieces—elastic panel 50, tape tab 62, and fastener patch 74—and the corresponding manufacturing steps needed to join those three pieces together and to chassis 14, closure members 38*a* be formed with fewer steps at the point of manufacturing diaper 10, resulting in a single nonwoven panel that includes both the elasticized portion and the hook fasteners. Further, unlike the prior art construction with a separate fastener patch bonded to a tape tab, the unitary hook fasteners are not subject to separation from the nonwoven panel.

Figure 10:
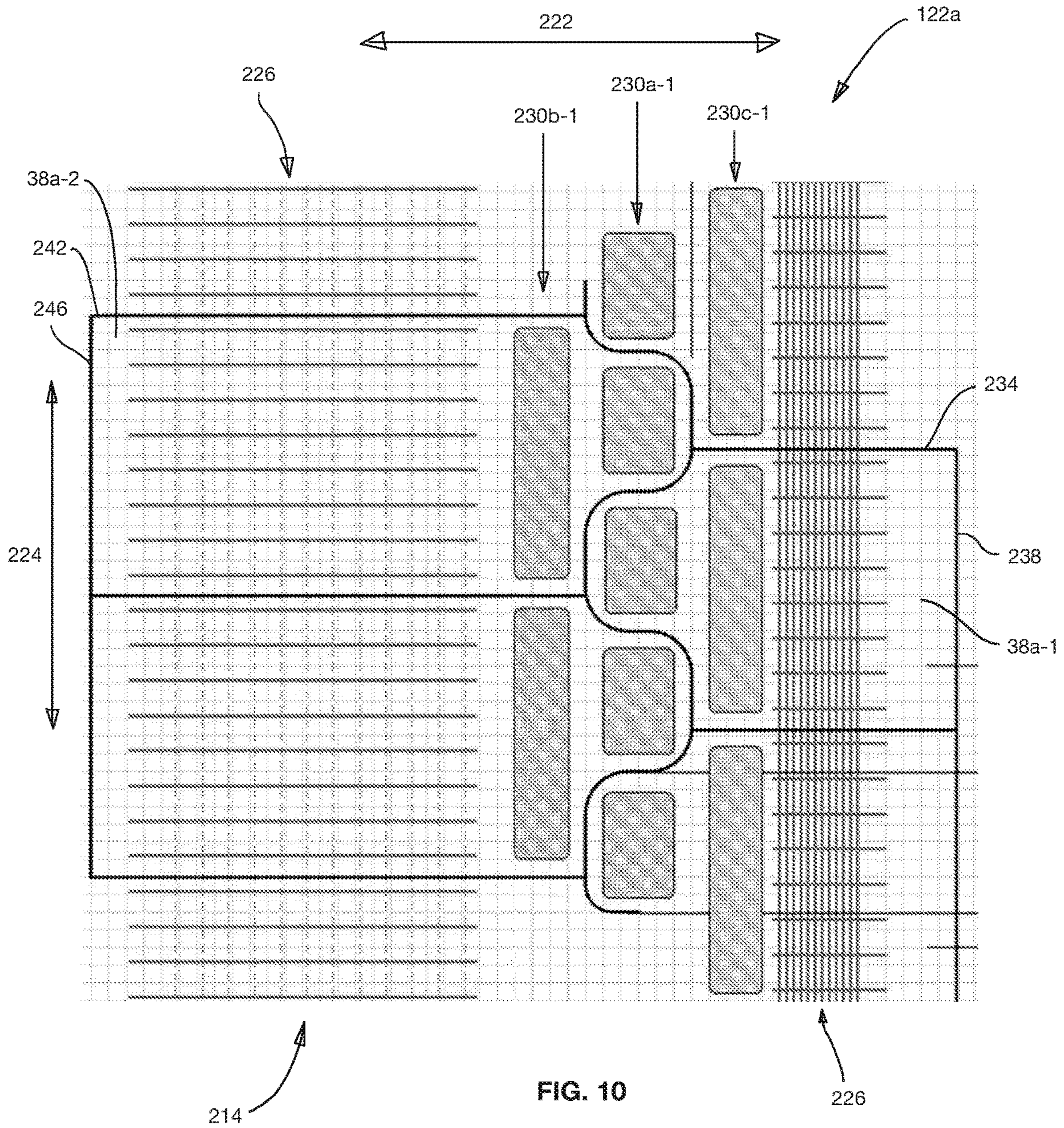
FIG. 10 depicts a plan view of a web of material, half of which is shown in a stretched state in which the elasticized portion is stretched, illustrating a second embodiment of a method of manufacturing fastener members that may be used in absorbent articles.
Figure 11:
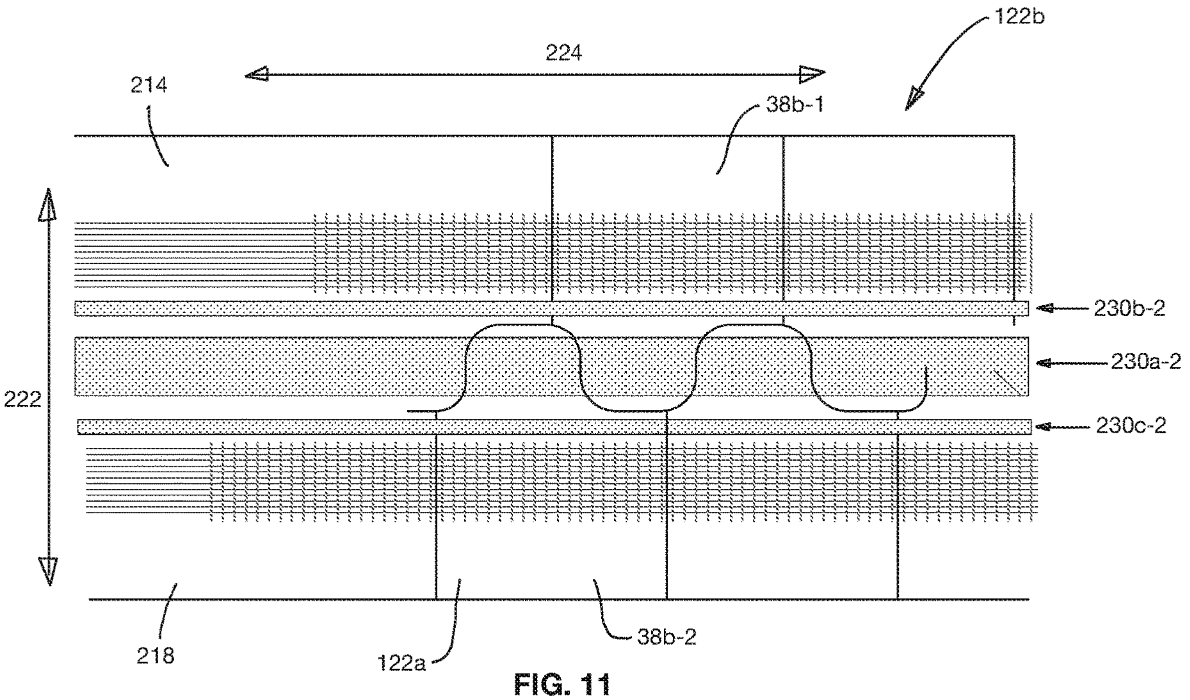
FIG. 11 depicts a plan view of a web of material, both halves of which are shown in a non-stretched state, illustrating a third embodiment of a method of manufacturing fastener members that may be used in absorbent articles.

Referring now to FIGS. 10 and 11; FIG. 10 depicts a plan view of a first web 122*a* of material, one half 214 of which is shown in a stretched state in which elasticized portion 194 is stretched; and FIG. 11 depicts a plan view of a second web 122*b* with both halves 214 and 218 in a non-stretched state. Webs 122*a* and 122*b* can each have a width, measured in direction 222, and a length, measured in direction 224, that is significantly longer than the width of the web. These webs can be provided with longitudinal elasticized regions 226 on either side of a longitudinal centerline of the web, and one or more fastener regions 230 having a plurality of hook fasteners that are unitary with the web. Elasticized regions 226 can be elasticized, via elastic strands and/or elastic film, before or after formation of the fastener region(s).

In the embodiments shown in FIGS. 10 and 11, the fastener regions include at least one medial fastener region; at least one first lateral fastener region on a first lateral side of the medial fastener region(s); and at least one second lateral fastener region on a second lateral side of the medial fastener region(s). For web 122*a* of FIG. 10, the at least one medial fastener region comprises a plurality of medial fastener regions 230*a*-1; the at least one first lateral fastener region comprises a plurality of first lateral fastener regions 230*b*-1; and the at least one second lateral fastener region comprises a plurality of second lateral fastener regions 230*c*-1. In contrast, for web 122*b* of FIG. 11, the at least one medial fastener region comprises a single medial fastener region 230*a*-2 spanning the entire length of the web; the at least one first lateral fastener region comprises a single first lateral fastener region 230*b*-2 spanning the entire length of the web; and the at least one second lateral fastener region comprises a single second lateral fastener regions 230*c*-2 spanning the entire length of the web.

The fastener region(s) of webs 122*a* and 122*b* can be formed by an embodiment the present methods. For example, some embodiments of the present methods suitable for forming fastener regions 230 comprise: disposing a nonwoven polymer web between a sonotrode, for example sonotrode 158, and a proximal surface of a tool defining a plurality of negative molds of hook fasteners, for example proximal surface 162 of tool 166, such that a first side, for example 170, of the web contacts the proximal surface of the tool. Such methods further comprise delivering ultrasonic energy from the sonotrode to the web such that a temperature of the first side of the web increases above the polymer's glass transition temperature; and compressing the web between the sonotrode and the tool such that polymer of the web flows into the cavities until the polymer substantially fills the cavities to form a plurality of hook fasteners on the first side of the web that are unitary with the web.

In the embodiment shown in FIGS. 10 and 11, rather than bonding a separate hook fastener material to web 122*a*, web 122*a* is disposed between a sonotrode and an appropriate tool, for example tool 166, and energy delivered and the web compressed as described above, to define a plurality of hook fasteners in three fastener regions 230*a*, 230*b*, 230*c* that extend the length of web 122*a* as shown. Tool 166, and specifically recesses 174 can be provided in a pattern corresponding to the desired pattern of fastener regions 190. For example, to form the fastener regions of web 122*a* shown in FIG. 10, tool 166 would include three periodically-interrupted rows of recesses 174 around the perimeter of tool 166, with the interruptions in the first row corresponding to the spaces between adjacent ones of first lateral fastener regions 230*b*-1, interruptions in the medial row corresponding to the spaces between adjacent ones of medial fastener regions 230*a*-1, and interruptions in the second lateral row corresponding to the spaces between adjacent ones of second lateral fastener regions 230*c*-1. In contrast, to form the fastener regions of web 122*b* shown in FIG. 11, tool 166 would include three substantially continuous rows of recesses 174 around the perimeter of tool 166, with the medial row being wider than the two lateral rows.

Some embodiments of the present methods further comprise cutting the web in at least one direction laterally across the or between the fastener region(s) 230 to define one or more fastener members each having a first end 54, a second end 70, and a plurality of fastener regions 74*a*. For example, each of lateral fastener regions 230*b*-1 and 230*c*-1 is elongated, and cutting web 122*a* comprises cutting along line 234 in the following sequential segments: laterally inward from a first lateral edge 238 of web 122*a;* laterally inward between a first one and second one of first lateral fastener regions 230*b*-1; around a first one of the medial fastener regions 230*a*-1; and laterally outward between the second one and a third one of first lateral fastener regions 230*b*-1; and laterally outward to first lateral edge 238 of web 122*a* to separate a first fastener member 38*a*-1 from the web. In some embodiments, cutting 122*a* further comprises cutting web 122*a* along line 242 in the following sequential segments: laterally inward from a second lateral 246 edge of the web; laterally inward between a first one and second one of second lateral fastener regions 230*c*-1; around a second one of medial fastener regions 230*a*-1; and laterally outward between the second one and a third one of second lateral fastener regions 230*c*-1; and laterally outward to second lateral edge 246 of web 122*a* to separate a second fastener member 38*a*-2 from the web. In this embodiment, in which portions of lines 234 and 242 are coincident, the cutting is such that there is no wasted web between first and second fastener members 38*a*-1 and 38*a*-2. The cutting pattern of web 122*b* shown in FIG. 11 is substantially similar, with the only different relative to that of web 122*a* being that fastener regions 230*a*-2, 230*b*-2, and 230*c*-2 are continuous along the length of web 122*b* such that the cutting extends across respective ones of the fastener regions to define closure members 38*b*-1, 38*b*-2, and so on, with slightly different fastener portions 202*a* and 202*b* that extend to the upper and lower edges of the respective nonwoven panel 198.

Some embodiments of the present methods further comprise coupling the first end of the fastener member to a front or rear waist portion of a chassis of a disposable absorbent article. For example, in the embodiment shown in FIGS. 10 and 11, once closure members 38*a* or 38*b* are separated from web 122*a* or 122*b,* respectively, first end 54*a* of each closure member can be bonded to rear waist portion 18 of a chassis 14.

In some embodiments of the present methods, the foregoing disposing, delivering, compressing, cutting, and bonding steps are performed on the same manufacturing floor and/or on the same manufacturing line. In particular, the formation of hook fasteners by the present methods permit the formation of the hook fasteners on the same manufacturing floor or even in the same manufacturing line on which the rest of the absorbent article is assembled. In contrast to prior art methods in which hook fastener materials are obtained from a supplier, or at least from a separate manufacturing facility or line, and bonded to tape tabs, the present methods permit the more-efficient option of on-site formation of hooks that are unitary with a web of material that would be included in the absorbent article anyway, thereby eliminating the need for the additional hook fastener material.

Figure 12:
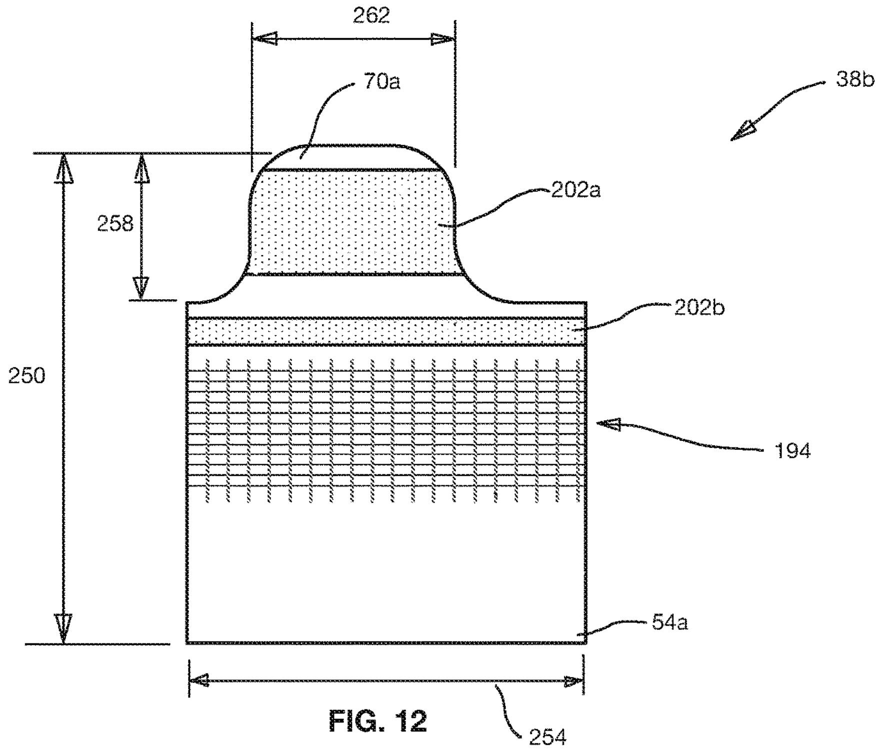
FIG. 12 depicts a plan view of a single fastener member made by the method of FIGS. 10 and 11.

FIG. 12 depicts a closure member 38*b* cut from web 122*b* shown in FIG. 11. The shape of the perimeter of nonwoven panel 194 and closure member 38*b* is substantially similar to that of closure member 38*a.* Closure member 38*b* has a width 250 between first end 54*a* and second end 70*a,* and a height 254. The width and height are described with reference to the orientation of the closure member when in use, specifically, when the width of the closure member horizontally extending circumferentially around a portion of a user's waist. As shown, a portion of closure member 38*b* adjacent second end 70*a,* with a width 258, has a height 262 that is smaller than height 254 of the majority of closure member 38*b*. In this configuration, the transition between the larger height (254) and the smaller height (262) is disposed between first fastener portion 202*a* and second fastener portion 202*b,* such that first fastener portion 202*a* has the relatively smaller height and second fastener portion 202*b* has the relatively larger height to reduce torque imparted to first fastener portion 202*a.*

Figure 1:
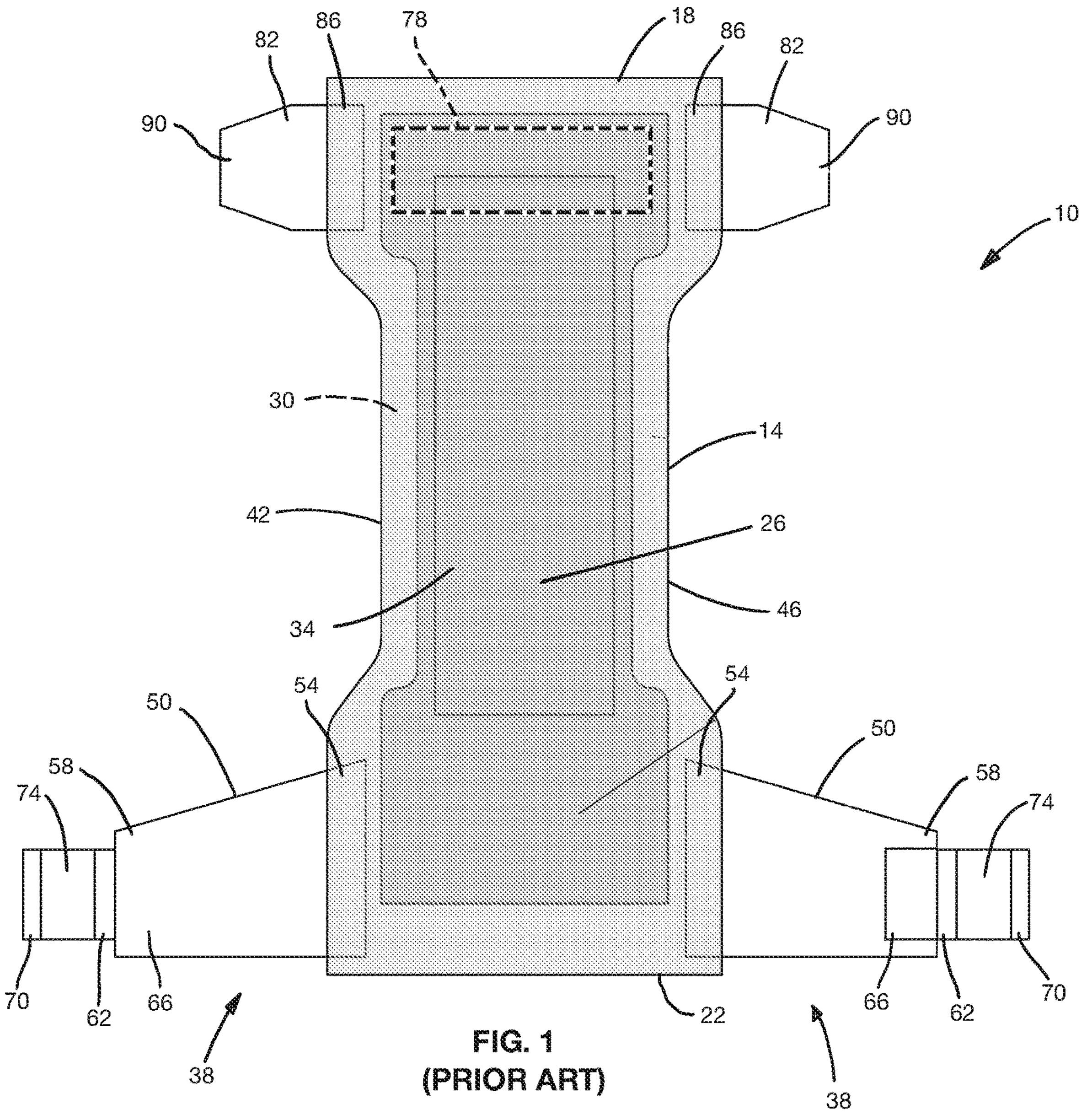
FIG. 1 depicts a top plan view of a prior art disposable absorbent article, specifically a diaper, in an open configuration.
Figure 2:
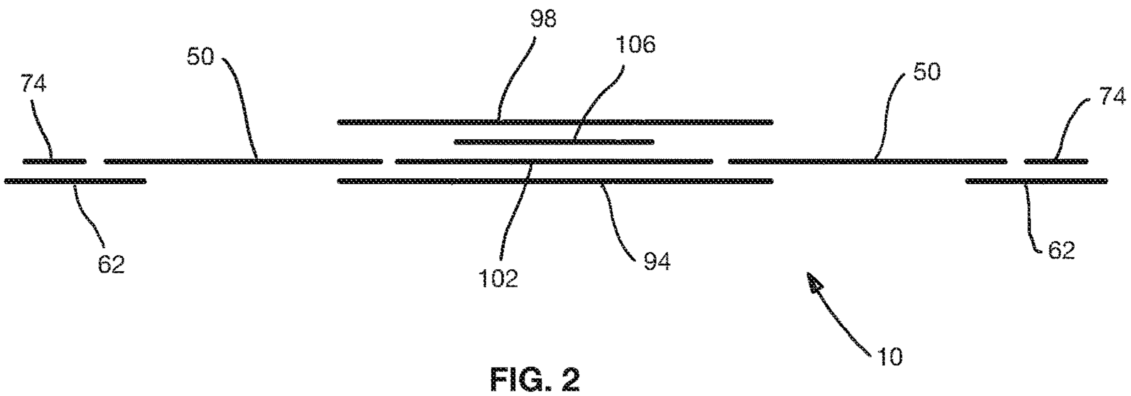
FIG. 2 depicts an exploded end view of the diaper of FIG. 1.
Figure 3:
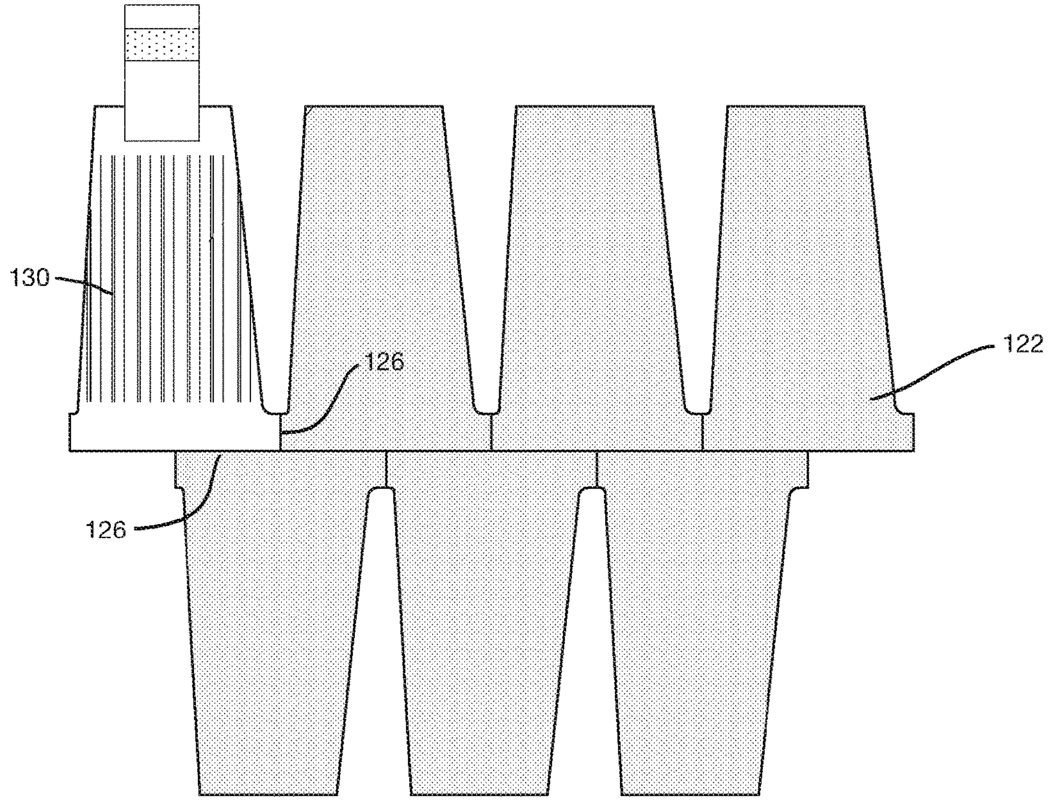
FIG. 3 depicts a plan view of an elasticized web of material illustrating a prior art method of manufacturing back ear closure members for the diaper of FIG. 1.
Figure 4:
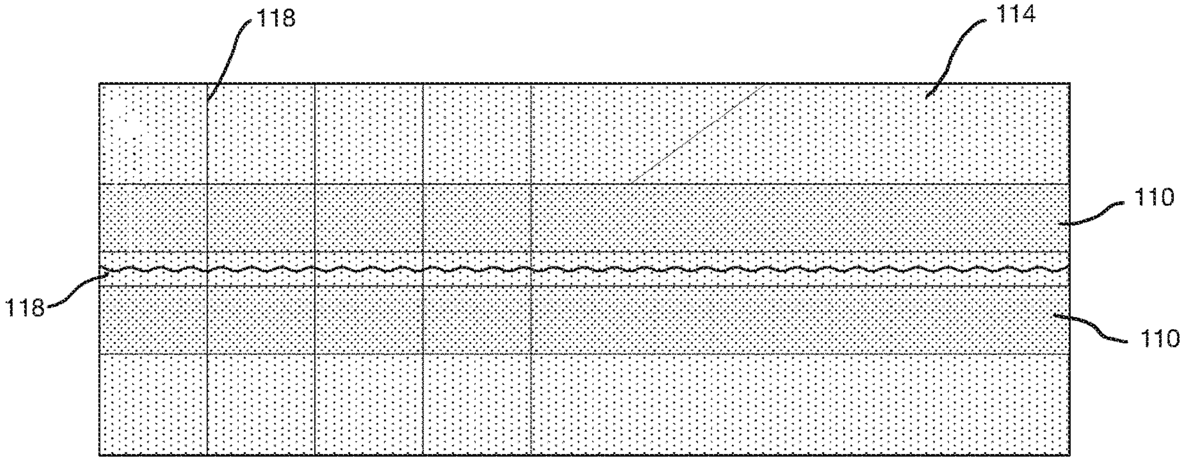
FIG. 4 depicts a plan view of a web of material illustrating a prior art method of manufacturing fastener members for the back ear closure members of FIG. 3.
Figure 5A:
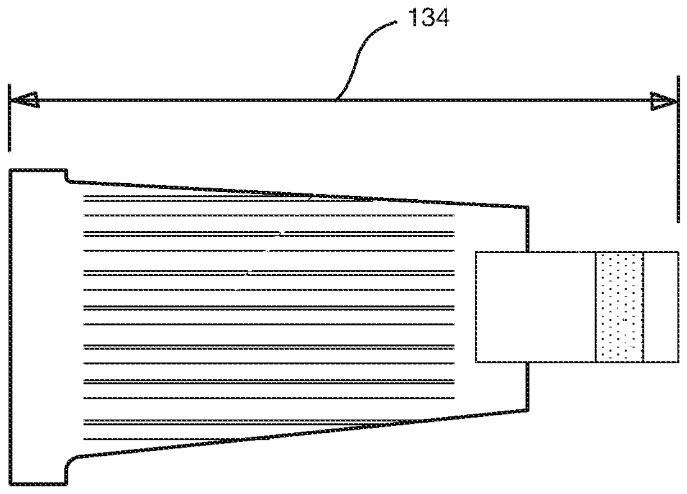
FIGS. 5A-5C depict plan views of a back ear closure member manufactured by the methods of FIGS. 3 and 4 for the diaper of FIG. 1.
Figure 5B:
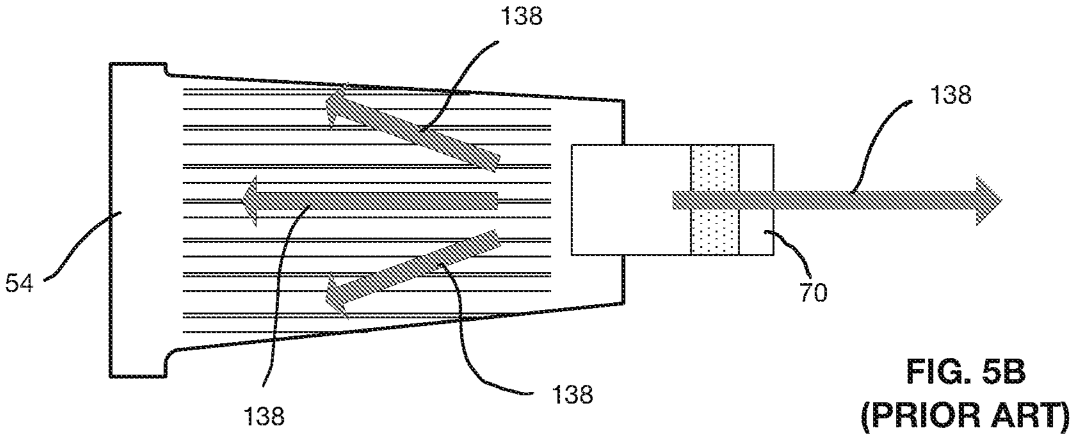
Figure 5C:
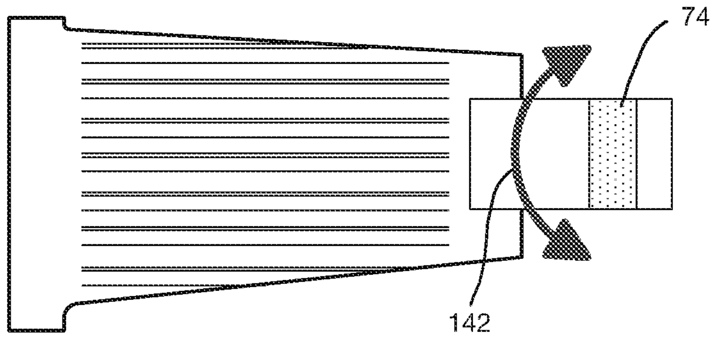
Figure 6:
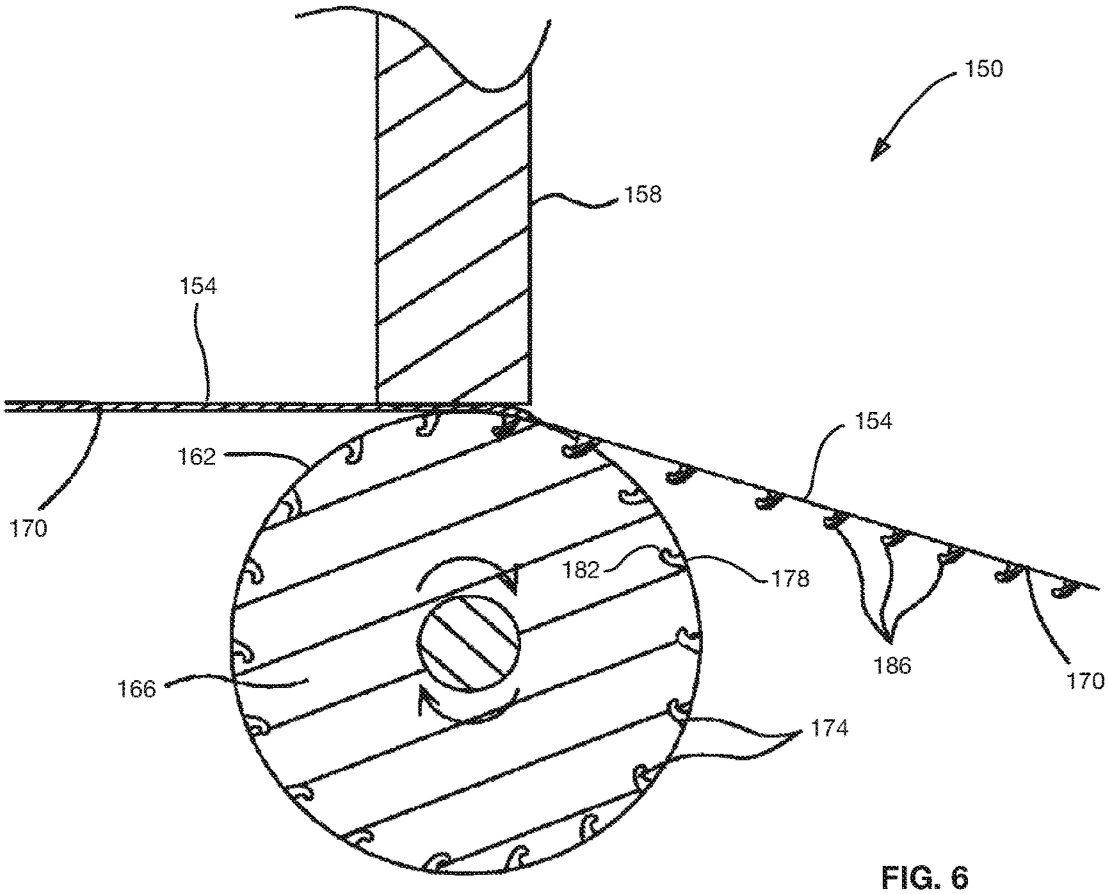
FIG. 6 depicts a conceptual side view of a prior art system for forming hook fasteners that are unitary with a web of material, such as a nonwoven.
Figure 13A:
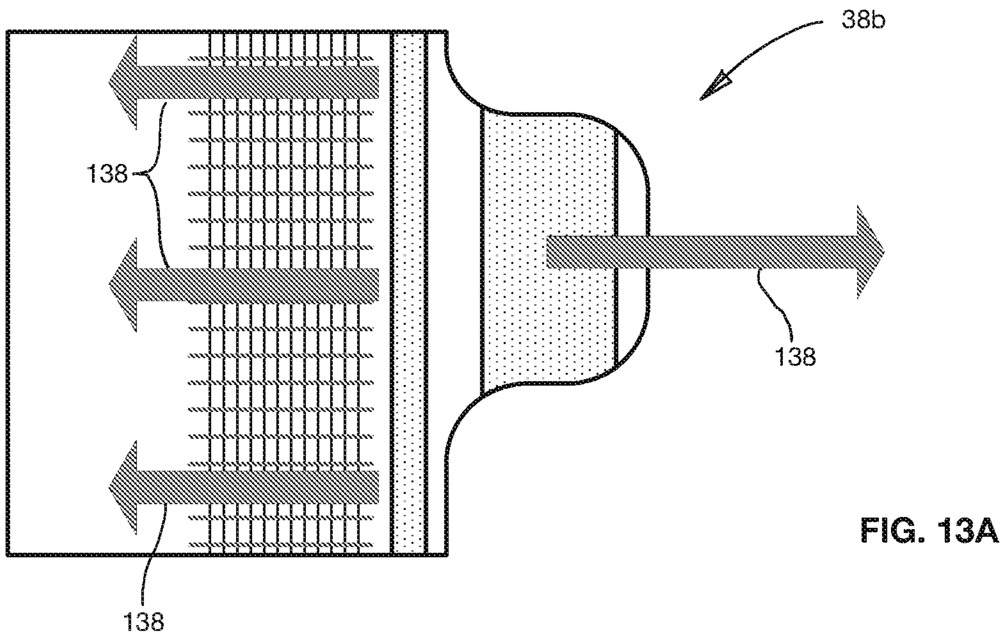
FIGS. 13A-13B depicts plan views of the fastener member of FIG. 11 showing certain forces to which the fastener member may be subjected when included in an absorbent article.
Figure 13B:
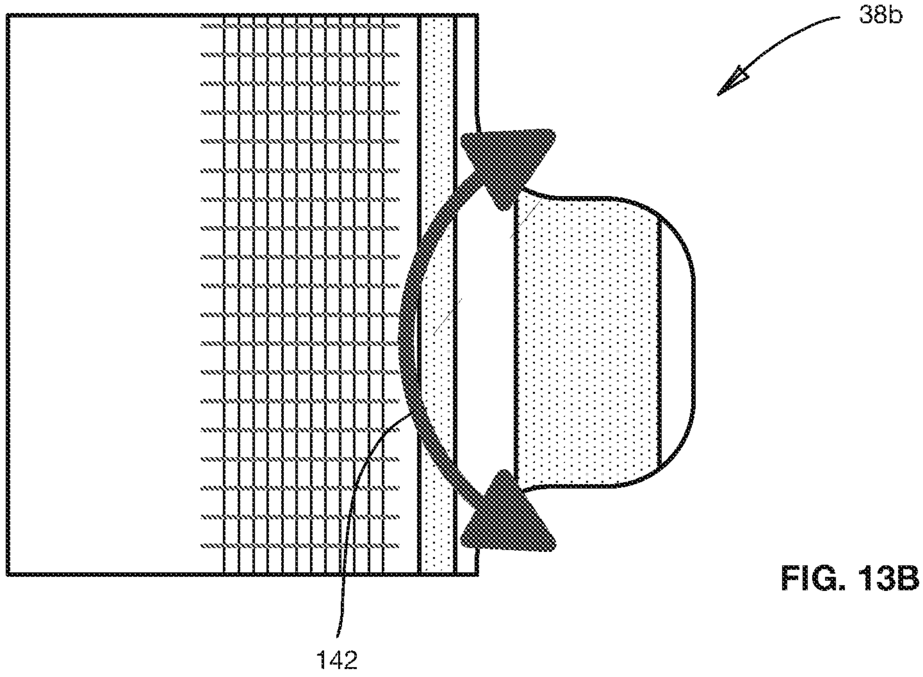

For example, as indicated by arrows 138 in FIG. 13A, the primary force to which closure member 38*b* is subjected during use is tension between first end 54*a,* at which the closure member is bonded to the rear waist portion, and second end 70*a,* at which the closure member is coupled to the front waist portion. However, as indicated by arrow 142 in FIG. 13B, closure member 38*b* may also be subject to torque around first fastener portion 202*a.* However, in contrast to the prior art design discussed above with reference to FIGS. 5A-5C, second fastener portion 202*b* also engages the front waist portion of the chassis to resists torque around first fastener portion 202*a,* and this purpose of resisting torque is furthered to an even greater degree by the larger height of second fastener portion 202*b* which allows second fastener portion to resist forces applied from any of a larger range of angles around first fastener portion. In this way, second fastener portion 202*b* results in more-even distribution of forces, relative to prior art closure member 38, at first end 54*a,* permitting the use of relatively smaller number of elastic strands 130, or elastic strands of smaller size or decitex, than may be required in the elastic panel (50) of the prior art closure member 38.

Figure 14:
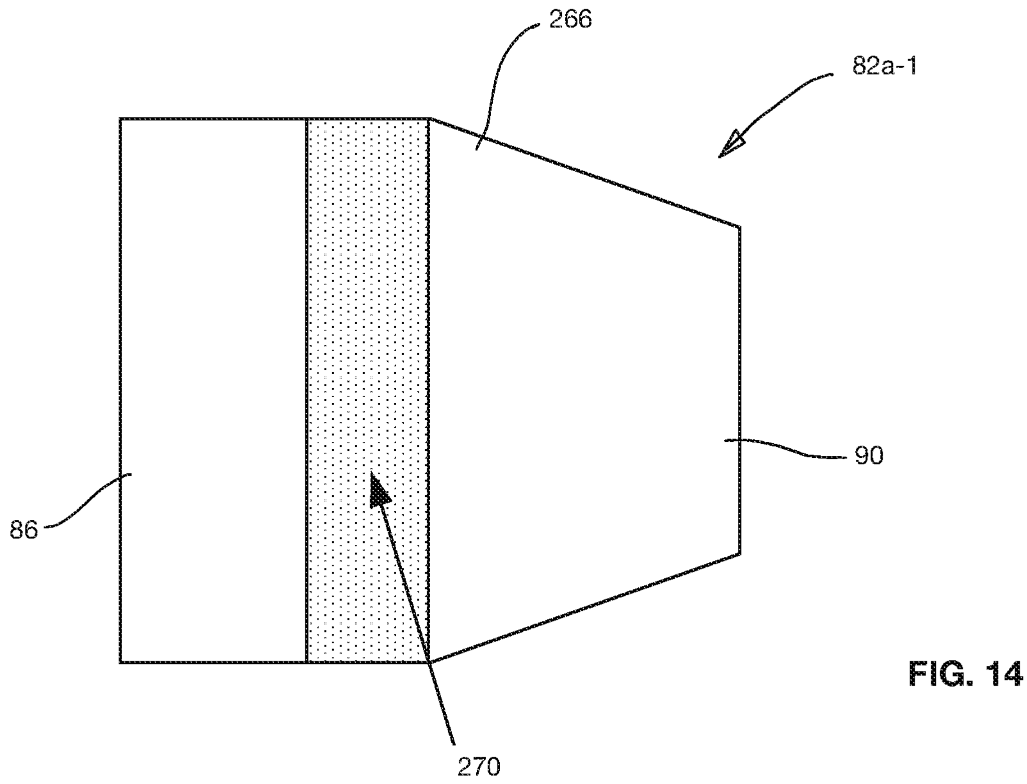
FIG. 14 depicts a plan view of a first embodiment of the present front-ear members, with a region of unitary hook fasteners.
Figure 15:
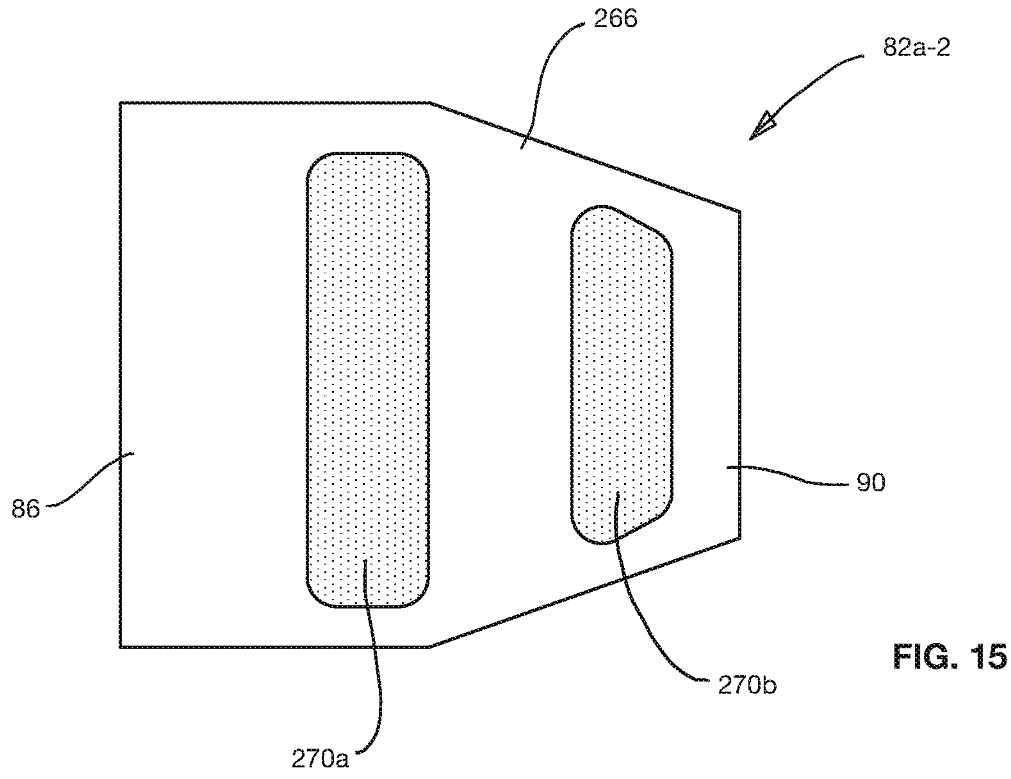
FIG. 15 depicts a plan view of a second embodiment of the present front-ear members, with two regions of unitary hook fasteners.
Figure 16B:
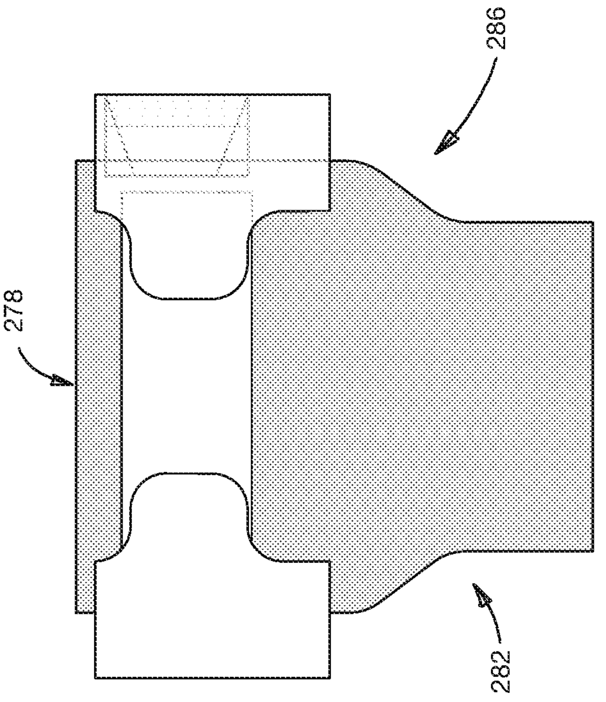
FIGS. 16A and 16B, respectively, depict open and closed configurations of the diaper of FIG. 8.
Figure 16A:
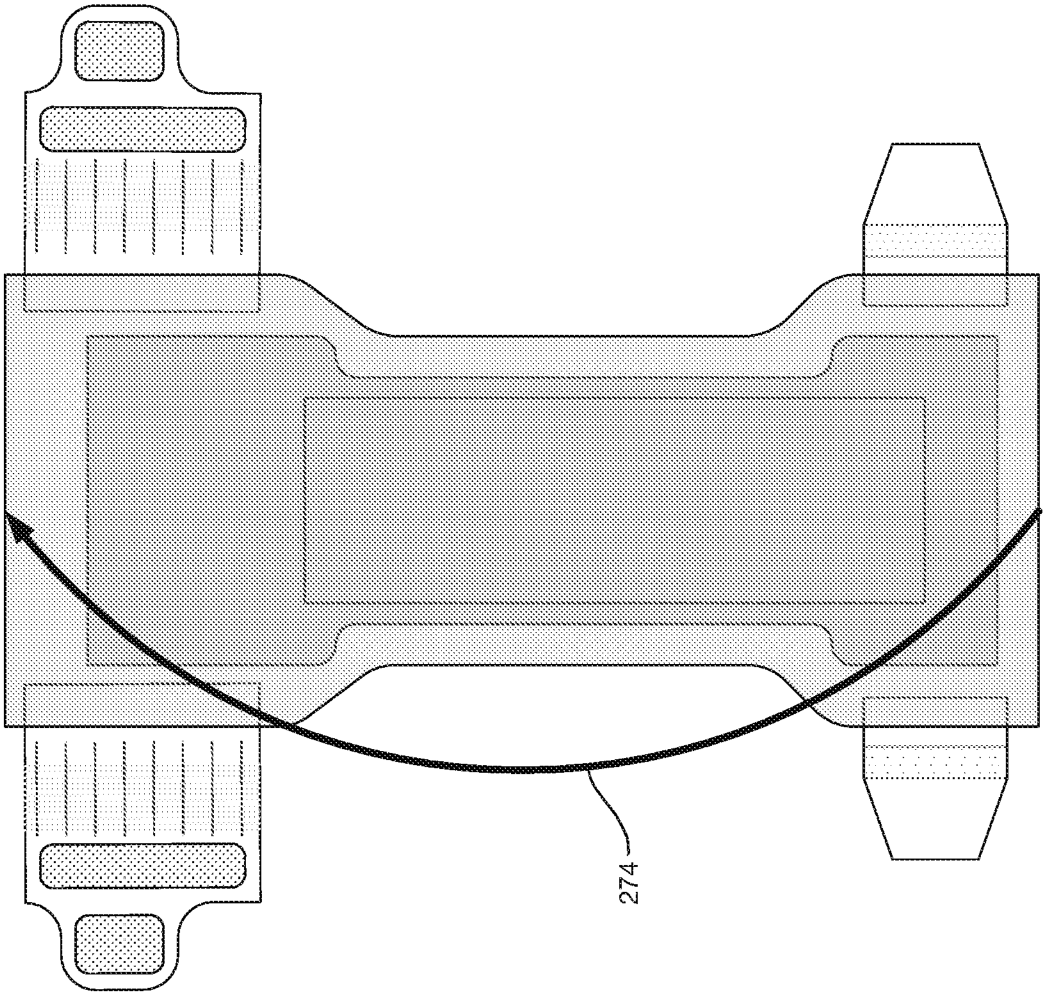
Figure 17B:
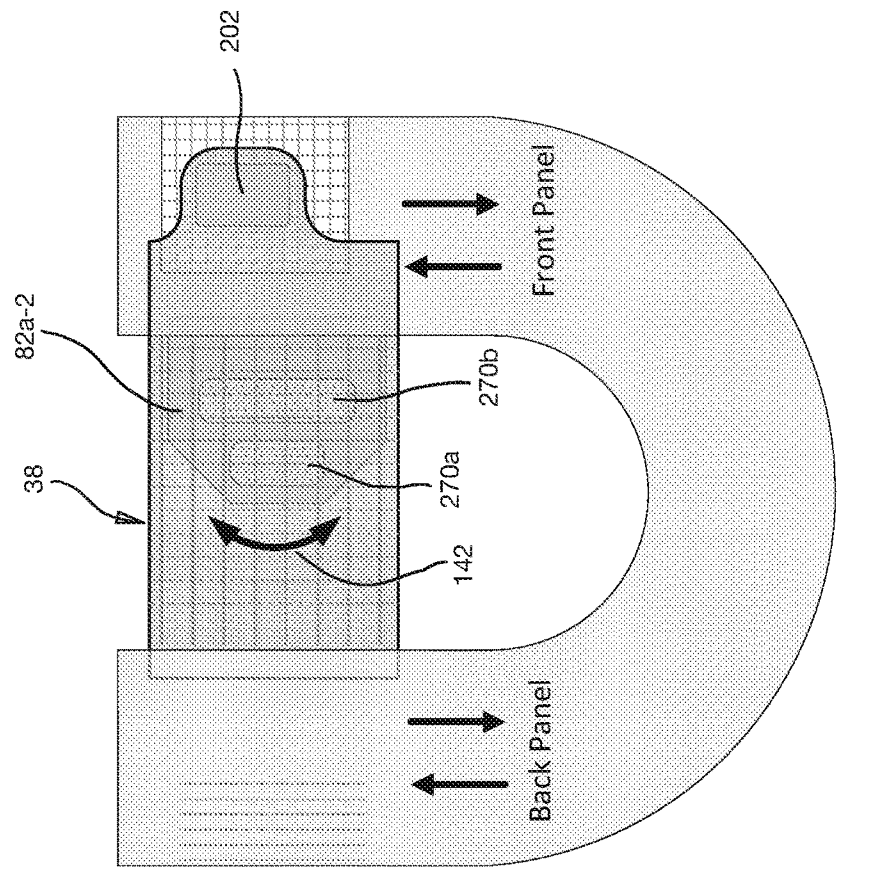
FIGS. 17A and 17B, respectively, depict side views of a prior art diaper and the diaper of FIG. 8 in closed configurations.
Figure 17A:
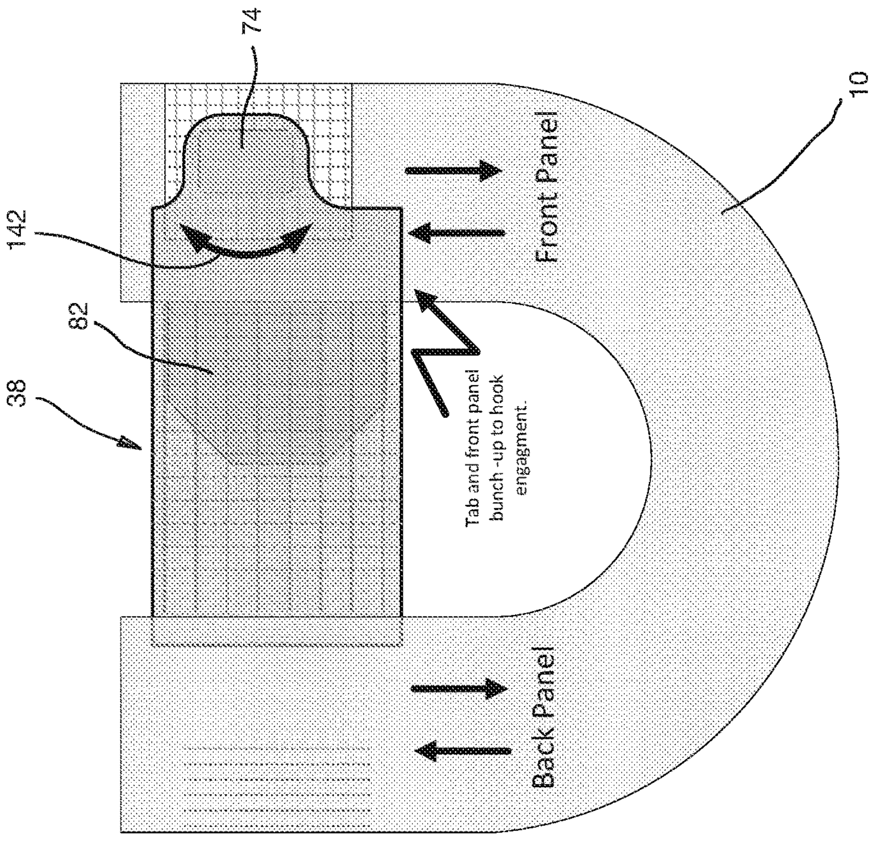

Referring now to FIGS. 14 and 15; FIG. 14 depicts a first embodiment 82*a*-1 of the present front-ear members with a region of unitary hook fasteners; and FIG. 15 depicts a second embodiment 82*a*-2 of the present front-ear members with two regions of unitary hook fasteners. Front-ear member 82*a*-1 includes a nonwoven panel 266 having a first end 86, a second end 90, and a fastener region 270 with a plurality of hook fasteners that are unitary with the nonwoven panel 266. Front-ear member 82*a*-1, and specifically fastener region 270, can be formed by methods similar to those described above for tape tabs 62*a* and closure members 38*a* and 38*b*. However, for front-ear member 82-1 the unitary hook fasteners are configured to engage the body facing side of the corresponding closure member 38, 38*a,* or 38*b* of the diaper, such that fastener region 270 is disposed on an outer side 30 of nonwoven panel 266. Front-ear member 82*a*-2 is substantially similar to front-ear member 82*a*-1, with two primary exceptions. First, the front-ear member 82*a*-2 includes a first fastener regions 270*a* and a second fastener region 270*b* disposed between first fastener region 270*a* and second end 90. Second, fastener regions 270*a* and 270*b* are spaced inwardly of the edges of nonwoven panel 266

Figure 18:
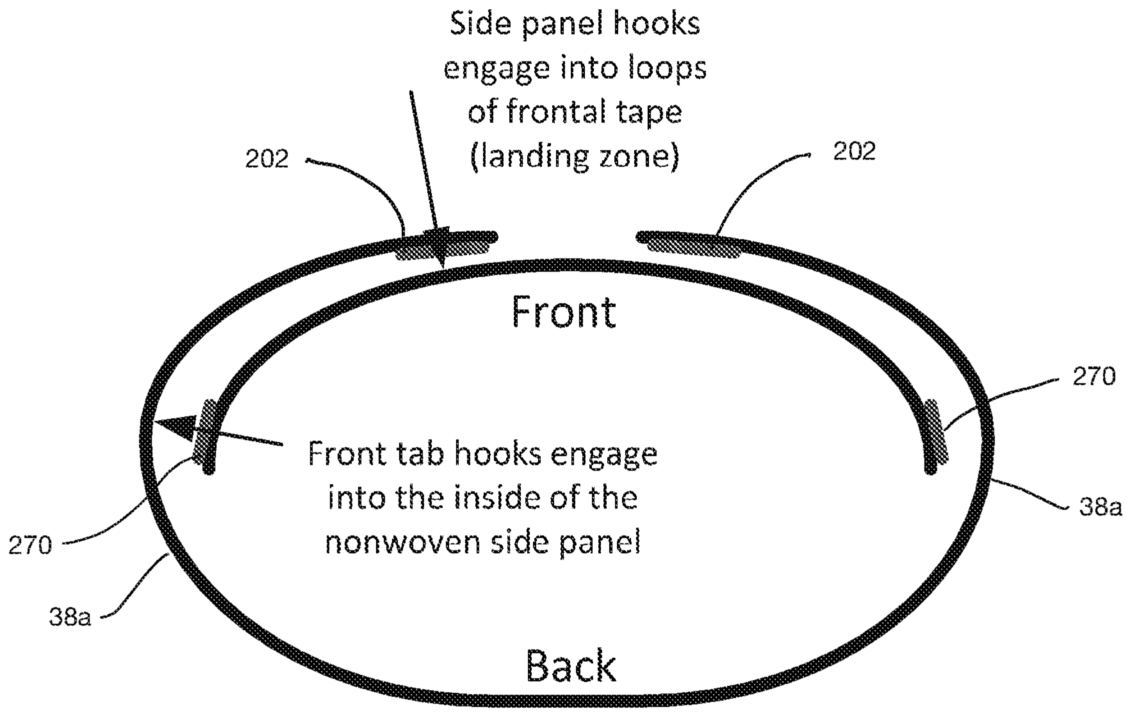
FIG. 18 depicts a top view of the diaper of FIG. 8 in a closed configuration.

Referring now to FIGS. 16A, 16B, 17A, 17B, and 18, various views of diaper 10*a* are shown to illustrate its closure for use and certain benefits relative to prior art diapers. Specifically, FIGS. 16A and 16B, respectively, depict open and closed configurations of diaper 10*a.* As indicated by arrow 274 in FIG. 16A, chassis 14 is folded to bring front waist portion 22 closer to the level of rear waist portion 18 and closure members 38*a* overlap and fastener portions 202*a* and 202*b* are releasably coupled to the front waist portion to define a closed configuration in which: the front and rear waist portions cooperate with the closure members to encircle and define a waist opening 278, a left side of the chassis defines a first leg opening 282, and a right side of the chassis defines a second leg opening 286. Additionally, FIGS. 17A and 17B, respectively, depict side views of a prior art diaper 10 and a variation of diaper 10*a* in closed configurations. As indicated by the relative positions of arrows 142 in the respective figures, the inclusion of front-ear member 82*a*-2, even in the absence of a second fastener region on closure member 38, resists torque on fastener region 202. Finally, FIG. 18 depicts a top view of diaper 10*a* in the closed configuration illustrating fastener regions 202 of closure members 38*a* releasably engaging the outer surface of the front waist portion, and fastener regions 270 of front-ear members 82*a*-1 releasably engaging the body facing surface of closure members 38*a*.

Figure 19:
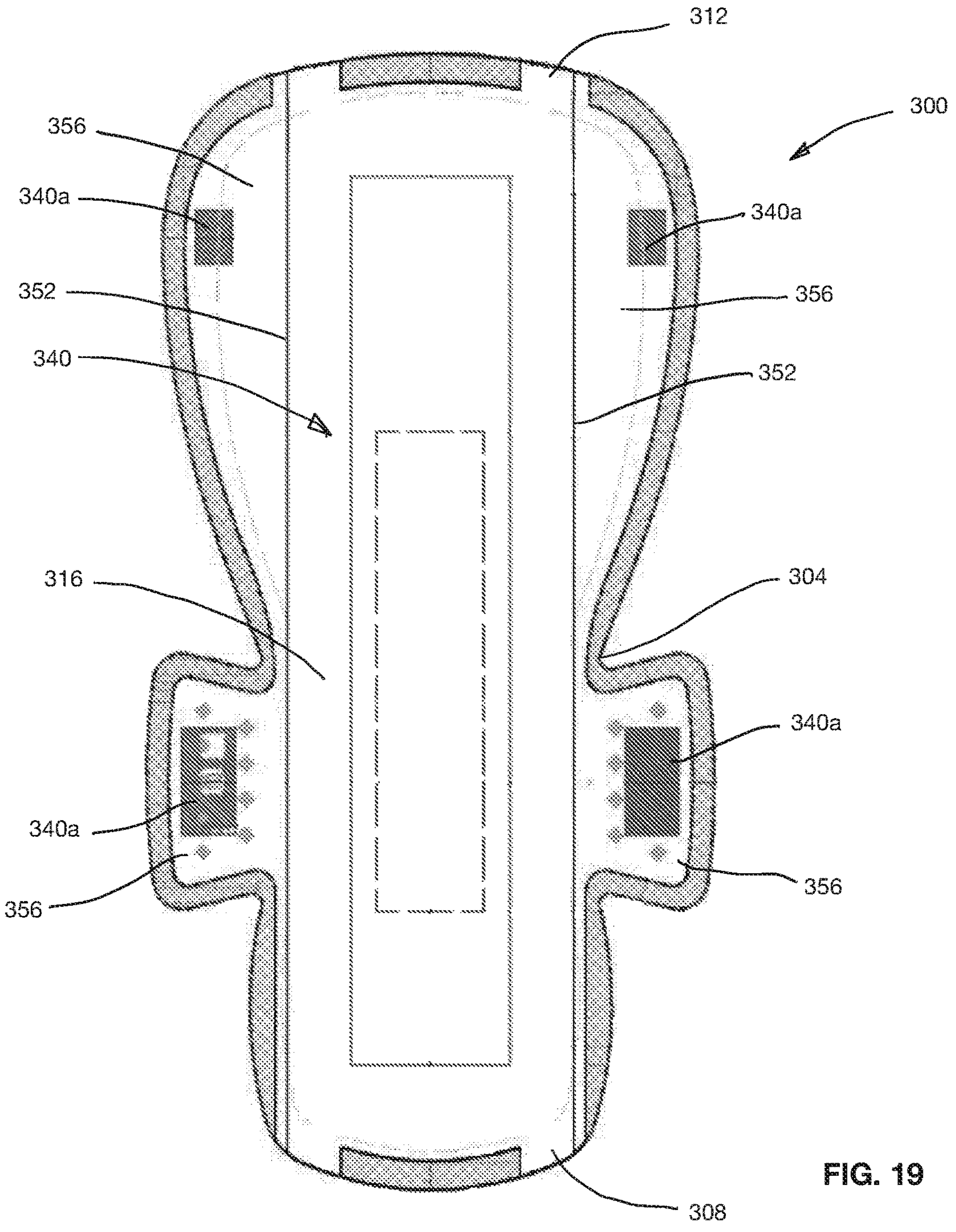
FIG. 19 depicts a bottom view of a first embodiment of the present disposable absorbent sanitary pad or liner articles.
Figure 20:
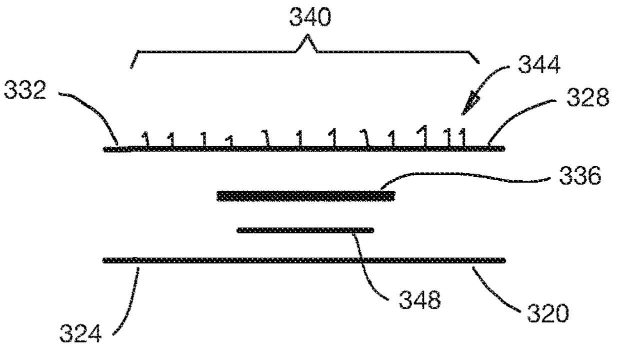
FIG. 20 depicts an exploded end view of the article of FIG. 19.

Some embodiments of the present disposable absorbent articles include disposable absorbent pads or liners for a garment with a backsheet having unitary hook fasteners on an outer surface of the backsheet. For example, FIGS. 19 and 20 depict one embodiment 300 of such a pad or liner. In this embodiment, pad 300 comprises: a chassis 304 having a front portion 308, a rear portion 312, and a crotch portion 316 between the front and rear portions. As shown in FIG. 20, chassis 304 including a liquid-permeable topsheet 320 having a body-facing side 324 configured to face a wearer when the article is in use, a liquid-impermeable backsheet 328 having an outer side 332 configured to face away from the wearer when the article is in use, and an absorbent core 336 disposed between the topsheet and the backsheet. Backsheet 328 comprises an outermost layer with at least one fastener region 340 on the outer side of the chassis, with each fastener region 340 comprising a plurality of hook fasteners 344 that are unitary with the outermost layer. Backsheet 328 can comprise one or more laminated layers. For example, when backsheet 328 comprises an inner film layer and an outer nonwoven layer, the unitary hook fasteners may be formed from both layers or only from the outer nonwoven layer, for example before the outer nonwoven layer is bonded to the inner film layer. In some embodiments, such as the one shown, pad 300 also includes an acquisition-distribution layer or “ADL” 348. As shown in FIG. 19, fastener region 340 spans a majority of a surface area of the outer side of the chassis, specifically the entire length of backsheet 328 between lateral boundaries 352. In this embodiment, pad 300 includes a plurality of fastener regions. Specifically, chassis 304 includes two pairs of optional lateral wing panels 356 with each lateral wing panel including an additional fastener region 340*a* with a plurality of unitary hook fasteners 344.

Figure 21:
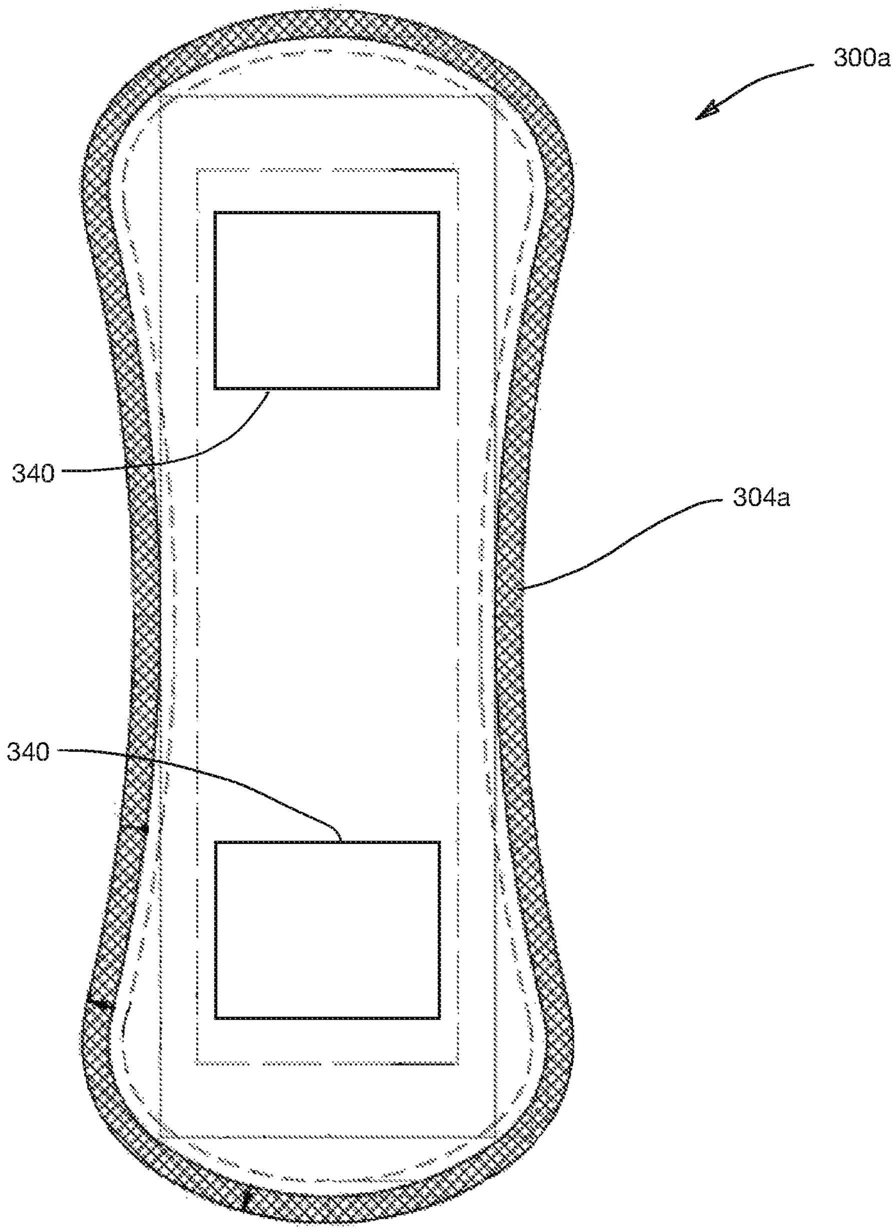
FIG. 21 depicts a bottom view of a second embodiment of the present disposable absorbent sanitary pad or liner articles.
Figure 22:
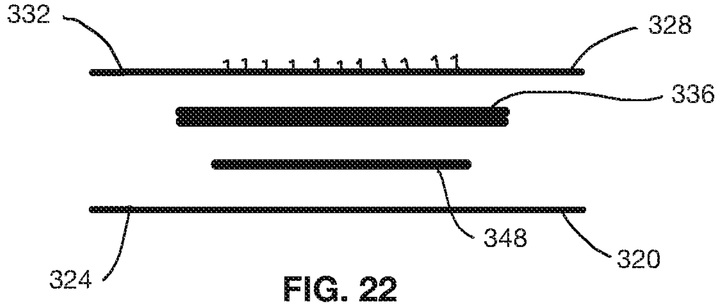
FIG. 22 depicts an exploded end view of the article of FIG. 21.

FIGS. 21 and 22 depict a second embodiment 300*a* of the present pads or liners. Pad 300 is substantially similar in many respects to diaper 10, and the differences in pad 300*a* relative to pad 300 will therefore be described here. Specifically, chassis 304*a* of pad 300*a* is simpler than that of pad 300 in that chassis 304*a* does not include lateral wing panels 356. Pad 300*a* also differs in that it includes a plurality of fastener regions 340, for example spaced along a length of the pad as shown.

In some embodiments of the present methods of making a pad or liner, the method comprises: disposing a nonwoven polymer web between a sonotrode, for example sonotrode 158, and a proximal surface of a tool defining a plurality of negative molds of hook fasteners, for example proximal surface 162 of tool 166, such that a first side, for example 170, of the web contacts the proximal surface of the tool. Such methods further comprise delivering ultrasonic energy from the sonotrode to the web such that a temperature of the first side of the web increases above the polymer’s glass transition temperature; and compressing the web between the sonotrode and the tool such that polymer of the web flows into the cavities until the polymer substantially fills the cavities to form a plurality of hook fasteners on the first side of the web that are unitary with the web.

Some embodiments of the present methods further comprise cutting the web in at least one direction laterally across the or between the fastener region(s) to separate a portion of the web that includes at least a portion of at least one of the fastener region(s). For example, the web can be cut to form a backsheet having the shape shown in FIG. 19 or the shape shown in FIG. 21.

Some embodiments of the present methods further comprise bonding the separated web portion to a liquid-permeable topsheet 328, with an absorbent core 336 disposed between the separated web portion and the liquid-permeable topsheet, to define a pad, for example 300 or 300*a*, such that the web portion forms a backsheet of the article, for example backsheet 320.

In some embodiments of the present methods of forming a pad or liner, the foregoing disposing, delivering, compressing, cutting, and coupling steps are performed on the same manufacturing floor and/or on the same manufacturing line. In particular, the formation of hook fasteners by the present methods permit the formation of the hook fasteners on the same manufacturing floor or even in the same manufacturing line on which the rest of the absorbent article is assembled. In contrast to prior art methods in which hook fastener materials are obtained from a supplier, or at least from a separate manufacturing facility or line, and bonded to tape tabs, the present methods permit the more-efficient option of on-site formation of hooks that are unitary with a web of material that would be included in the absorbent article anyway, thereby eliminating the need for the additional hook fastener material. Additionally, for pads of the type shown in FIGS. 19 and 21, the fastener portions 340 would typically include adhesive and need to be covered by a release strip to prevent the adhesive from sticking to surfaces or collecting lint prior to use. Thus, the inclusion of unitary hook fasteners can simplify the construction of the pad or liner by eliminating the manufacturing steps or processes, and materials, associated with conventional adhesives and release strips.

Figure 23:
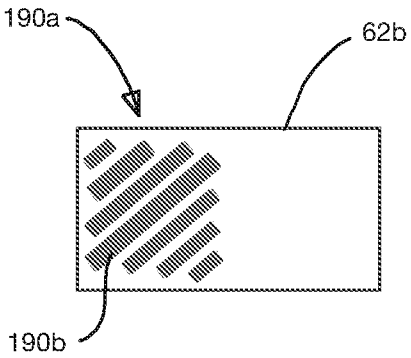
FIG. 23 depicts an enlarged plan view of an additional embodiment of the present tape tabs for diapers and adult incontinence briefs.

FIG. 23 depicts an enlarged plan view of an additional embodiment 62*b* of the present tape tabs for diapers and adult incontinence briefs. Tape tab 62*b* is substantially similar to tape tab 62*a*, with the primary exception that the fastener region 190*a* includes a plurality of distinct sub-regions 190*b*. Specifically, in the embodiment shown, sub-regions 190*b* include elongated areas of unitary hook fasteners that extend at an angle relative to the width (horizontal in the depicted configuration) of the tape tab. In other embodiments, these elongated areas may be parallel or perpendicular to the width of the tape tab. In those of the present embodiments in which a fastener region includes a plurality of distinct sub-regions, the edge or boundaries of the sub-regions have an overall length that is greater than fastener region with a single perimeter, which increase in edge or boundary length can increase the tensile strength of the fastener region in use, and thereby the ability of the fastener region to reliably engage a material such a loop fasteners and/or to resist unintended separation.

Figure 24:
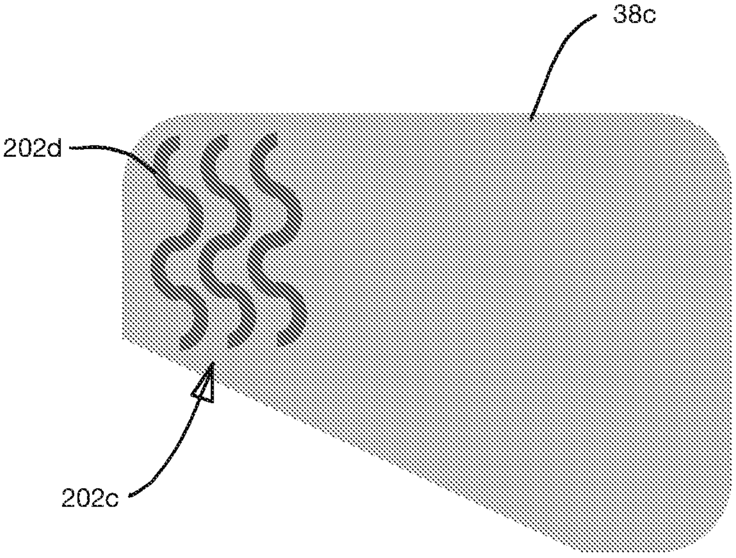
FIG. 24 depicts an enlarged plan view of an additional embodiment of the present closure members for diapers and adult incontinence briefs.

FIG. 24 depicts an enlarged plan view of an additional embodiment 38*c* of the present closure members for diapers and adult incontinence briefs. Closure member 38*c* is substantially similar to closure members 38*a* and 38*b*, with the primary exception that closure member 38*b* includes a fastener region 202*c* that includes a plurality of distinct sub-regions 202*d*. Specifically, in the embodiment shown, sub-regions 202*d* include elongated, curved or corrugated areas of unitary hook fasteners that extend generally perpendicular to the width (horizontal in the depicted configuration) of the tape tab. In other embodiments, sub-regions 202*d* may be angled or parallel to the width of the closure member. Further, sub-regions 202*d* may in other configurations be shaped similarly to sub-regions 190*b* of tape tab 62*b*.

Figure 25:
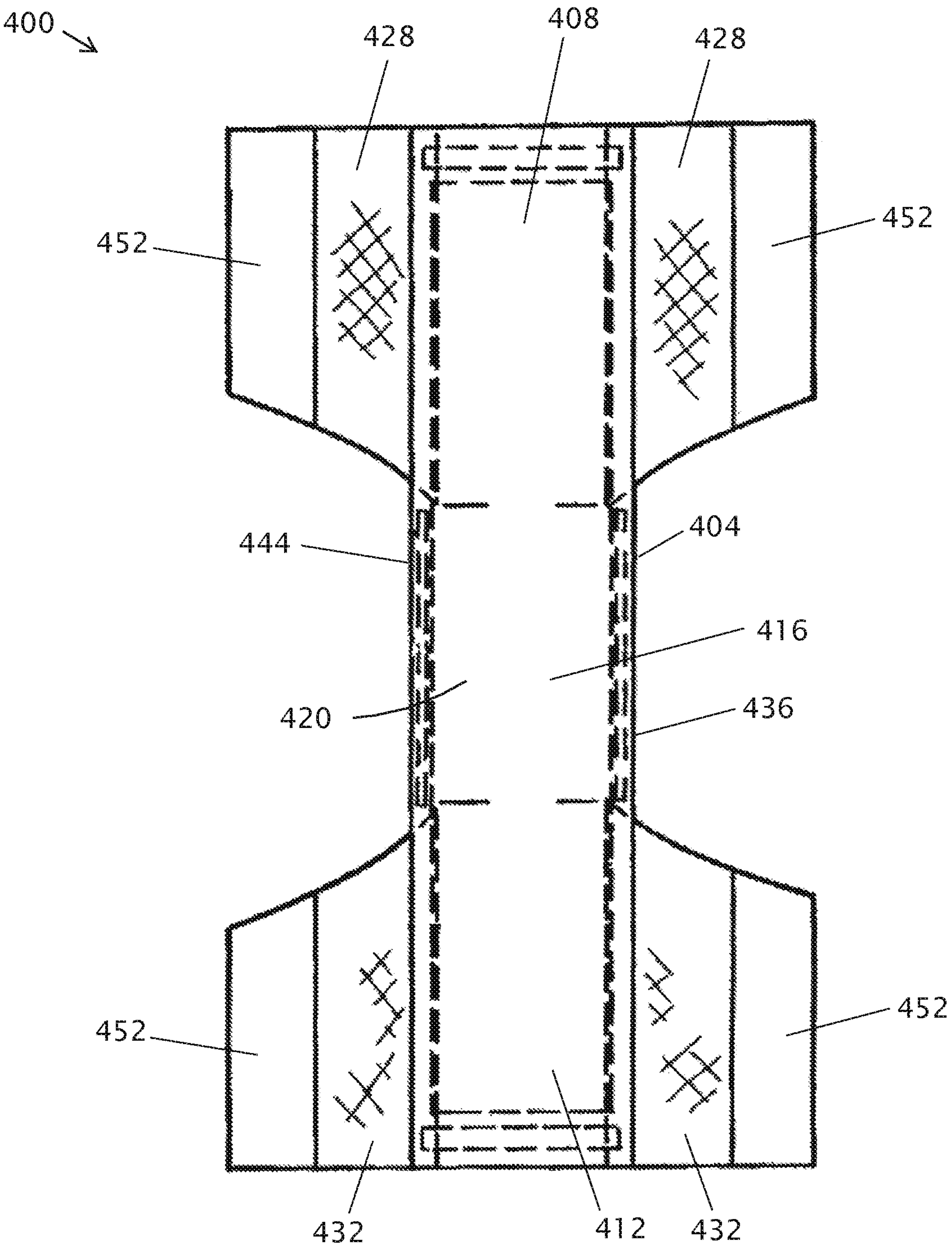
FIG. 25 depicts a bottom plan view of a disposable absorbent article, specifically a training pant, in an open configuration.
Figure 26:
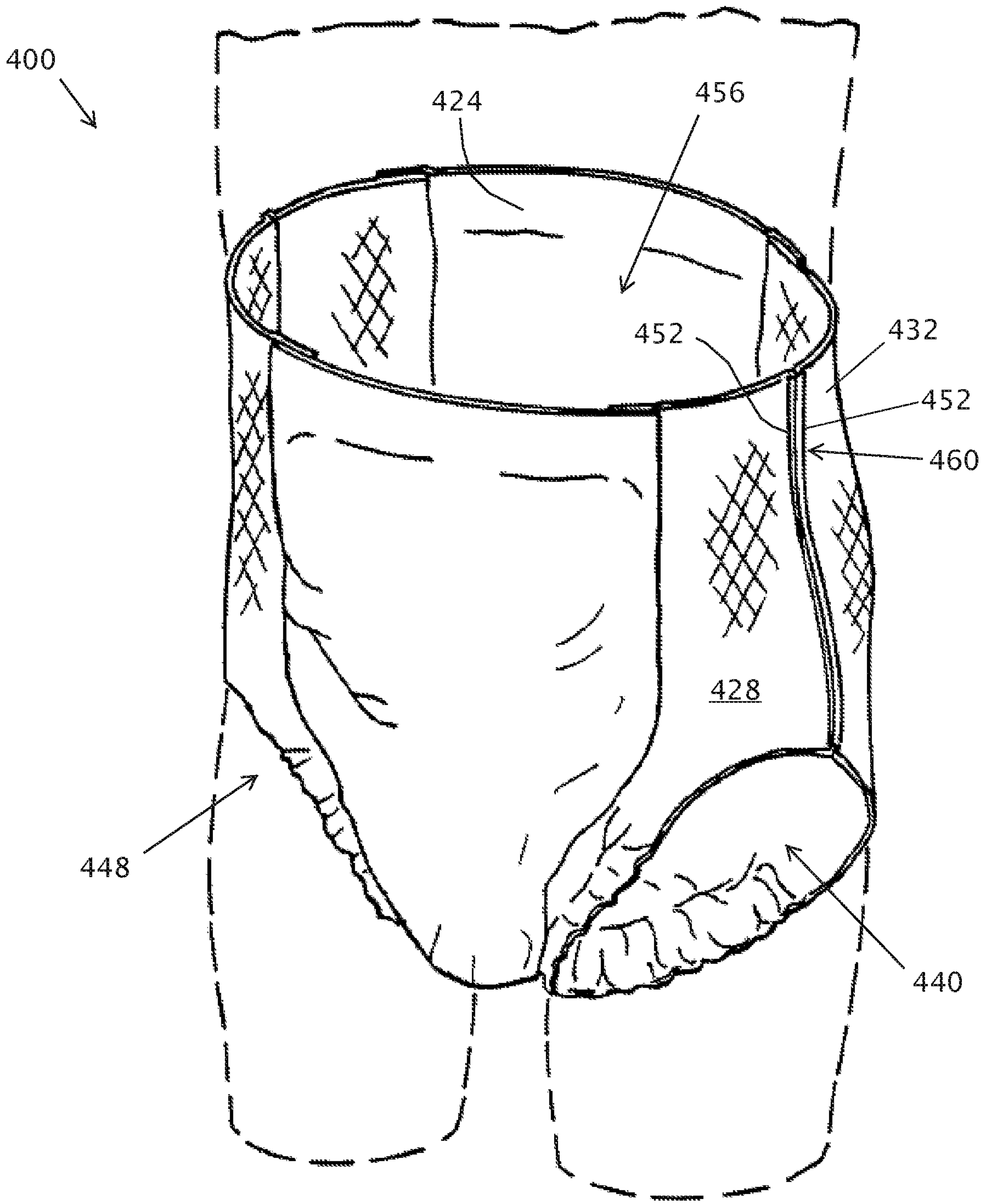
FIG. 26 depicts a perspective view of the training pant of FIG. 25 in a closed configuration.

Referring now to FIGS. 25 and 26, shown is one example of an additional type of disposable absorbent article into which unitary hook fasteners can be incorporated. By way of reference, U.S. Pat. No. 9,398,986 discloses certain prior art examples of training pants, and U.S. Pat. Nos. 6,976,978 and 4,940,464 disclose certain prior art examples of disposable incontinence garments or training pants. In the present embodiment depicted in FIGS. 25 and 26, training pant 400 includes a chassis 404 having a front waist portion 408, an opposing rear waist portion 412, and a crotch portion 416 extending longitudinally between front and rear waist portions 408, 412. Chassis 404 further includes an outer surface 420 configured to face away from a wearer during use of the diaper, and an opposing body facing surface 424 configured to face a wearer during use of the diaper.

As shown in FIGS. 25-26, training pant 400 further includes a pair of front elastic side panels 428 and a pair of rear elastic side panels 432 configured to couple rear waist portion 412 to front waist portion 408 in a well-known configuration in which a left side 436 of the chassis defines a first leg opening 440 for a wearer's left leg, and in which a right side 444 of the chassis defines a second leg opening 448 for the wearer's right leg. In the depicted configuration, each of side panels 428, 432 includes a connection portion 452 configured to be coupled to a connection portion 452 of another of side panels 428, 432. Specifically, connection portion 452 of the left one of front side panels 428 is configure to be coupled to connection portion 452 of the left one of rear side panels 432, and connection portion 452 of the right one of front side panels 428 is configure to be coupled to connection portion 452 of the right one of rear side panels 432, such that the waist portions 408, 412 and side panels, 428, 432 cooperate to define a waist opening 456 as shown in FIG. 26. Connection portions 452 of the respective side panels are configured to be removably coupled together via the present unitary hook fasteners to define a refastenable or adjustable side seam.

Figure 27B:
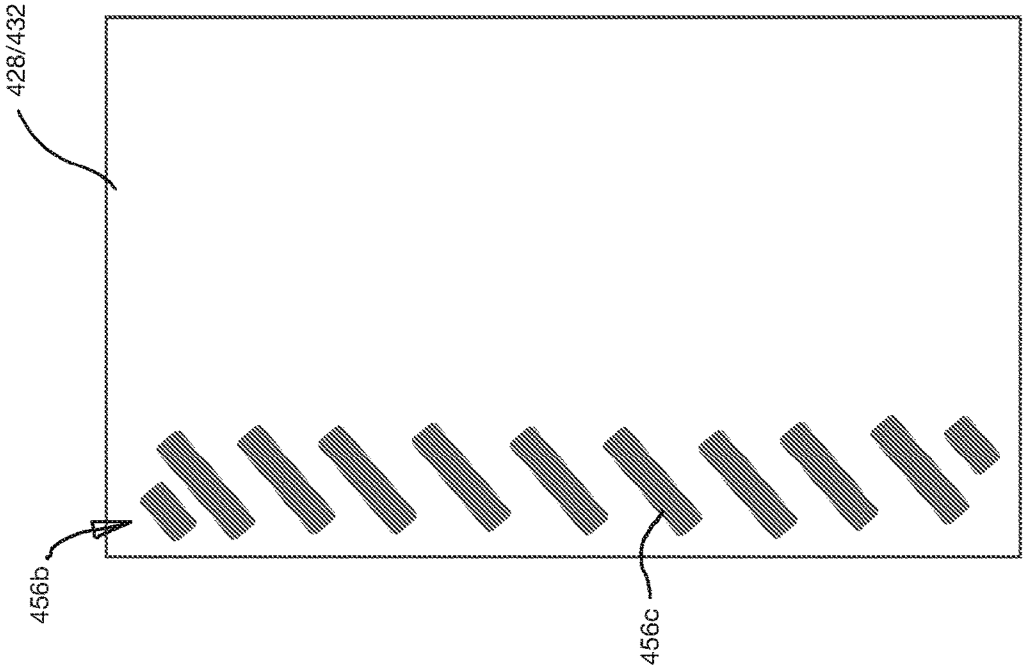
FIGS. 27A and 27B depict enlarged plan views of nonwoven connection portions for the training pant of FIGS. 25 and 26.
Figure 27A:
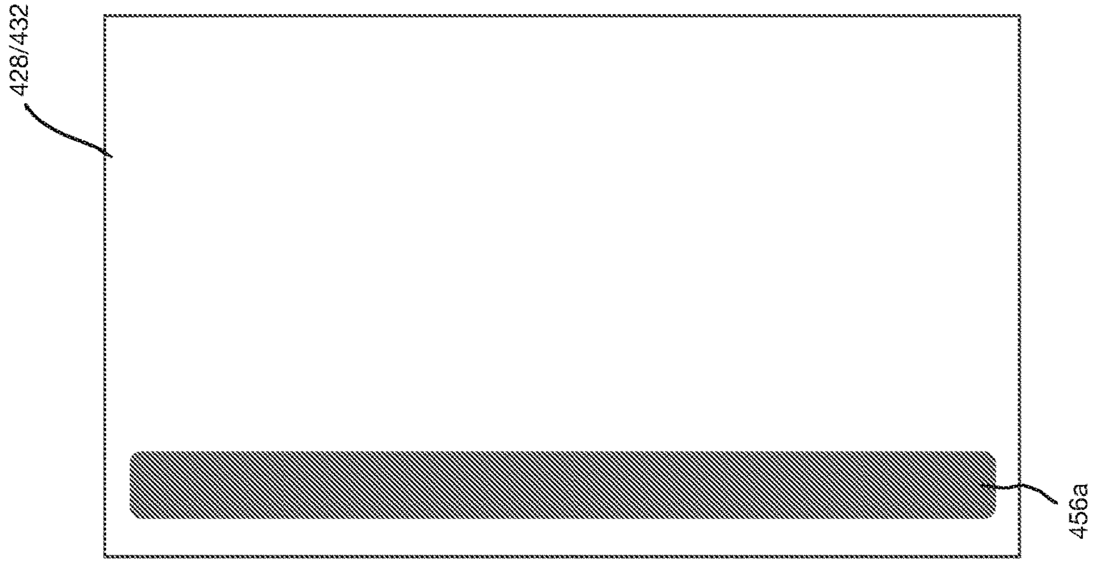

FIGS. 27A and 27B depict enlarged plan views of nonwoven side panels 428, 432 with unitary connection portions 452 for training pants such as training pant 10 of FIGS. 25 and 26. In each of these embodiments, a portion of the nonwoven side panel is elasticized, such as with a film or elastic strands, and a portion of the nonwoven panel is subject to the present methods to define unitary hook fasteners. For example, in the embodiment shown in FIG. 27A, the connection portion comprises a fastener region 456*a* that extends a majority of a height of the panel, whereas in the embodiment of FIG. 27B, the connection portion comprises a fastener region 456*b* that includes a plurality of distinct sub-regions 456*c* of the unitary hook fasteners. Specifically, in the embodiment of FIG. 27B, sub-regions 456*c* include elongated areas of unitary hook fasteners that extend at an angle relative to the width (horizontal in the depicted configuration) of the tape tab. In other embodiments, these elongated areas may be parallel or perpendicular to the width of the tape tab, or may be curved or corrugated as with sub-regions 202*c* described above. Front side panels 428 and/or rear side panels 428—for example only front side panels 428, only rear side panels 432, or both front and rear side panels 428, 432—can include fastener regions 456*a* or 456*b*/456*c*. In those of the present embodiments in which a fastener region includes a plurality of distinct sub-regions, the edge or boundaries of the sub-regions have an overall length that is greater than fastener region with a single perimeter, which increase in edge or boundary length can increase the tensile strength of the fastener region in use, and thereby the ability of the fastener region to reliably engage a material such a loop fasteners and/or to resist unintended separation.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A disposable absorbent article comprising:

a chassis having opposing front and rear waist portions, a crotch portion extending longitudinally between the front and rear waist portions, a body facing surface configured to face a wearer during use of the article, and an outer surface configured to face away from a wearer during use of the article;

two nonwoven front-ear members each having a first end, a second end, and a width extending between the first and second ends, each of the front-ear members having at least one fastener region on an outward-facing side of the front-ear member, each fastener region comprising a plurality of hook fasteners that are unitary with the nonwoven front-ear panel such that the hook fasteners and nonwoven front-ear panel are both formed by a common piece of nonwoven material that is bonded directly to the chassis;

two closure members each having a first end, a second end, and a width extending between the first and second ends, each of the closure members having an elasticized portion and a nonwoven panel with at least one fastener region on a body facing side of the nonwoven panel, each fastener region comprising a plurality of hook fasteners;

where the first end of each closure member is bonded to the rear waist portion of the chassis, and the second end of each closure member is configured to overlap and be releasably coupled to the front waist portion to define a closed configuration in which:

the front and rear waist portions cooperate with the closure members to encircle and define a waist opening, a left side of the chassis defines a first leg opening, and a right side of the chassis defines a second leg opening; and where the first end of each front-ear member is bonded to the front waist portion of the chassis, and the second end of each closure member is configured to be overlapped by and be releasably coupled to a body-facing side of a corresponding one of the closure members when the closure members are coupled to the front waist portion.

2. The article of claim 1, where each fastener region comprises a plurality of distinct sub-regions of the hook fasteners.

3. The article of claim 1, where a landing portion of the outer surface on the front waist portion of the chassis is configured to be releasably engaged by the fastener portions of the closure members.

4. The article of claim 3, where the portion of the outer surface is defined by an anchoring member bonded to a backsheet of the chassis.

5. The article of claim 4, where the anchoring member comprises a loop fastener material.

6. A disposable absorbent article comprising:

a chassis having opposing front and rear waist portions, a crotch portion extending longitudinally between the front and rear waist portions, a body facing surface configured to face a wearer during use of the article, and an outer surface configured to face away from a wearer during use of the article;

two rear closure members each having a first end, a second end, and a width extending between the first and second ends, and a height extending perpendicular to the width, each of the rear closure members comprising an elasticized portion and a nonwoven panel;

two front closure members each having a first end, a second end, and a width extending between the first and second ends, and a height extending perpendicular to the width, each of the front closure members comprising an elasticized portion and a nonwoven panel;

where the first end of each rear closure member is bonded to the rear waist portion of the chassis, the first end of each front closure member is bonded to the front waist portion of the chassis, and the second end of each rear closure member is configured to overlap and be releasably coupled to the second end of a corresponding one of the front closure members to define a closed configuration in which:

the front and rear waist portions cooperate with the front and rear the closure members to encircle and define a waist opening, a left side of the chassis defines a first leg opening, and a right side of the chassis defines a second leg opening; and where each of the front closure members and/or the rear closure members includes at least one fastener region on the respective nonwoven panel, each fastener region comprising a plurality of hook fasteners that are unitary with the nonwoven panel such that the hook fasteners and nonwoven panel are both formed by a common piece of nonwoven material that is bonded directly to the chassis, and configured to releasably couple the second end of each front closure member to the second end of the corresponding one of the front closure members.

7. The article of claim 6, where each of the fastener regions comprises a plurality of distinct sub-regions of the hook fasteners.

8. The article of claim 6, where the elasticized portion of each of the closure members is defined by an elastic panel having a first end defining the first end of the closure member, a second end, and a width extending between the first and second ends, and the nonwoven panel of each of the closure members has a first end bonded to the elastic panel, and a second end defining a second end of the closure member such that the width of the closure member extends from the first end of the elastic panel to the second end of the fastener tab.

9. The article of claim 6, where the nonwoven panel of each of the closure members includes the respective elasticized portion.

* * * * *